United States Patent [19]
Yoon

[11] Patent Number: 5,571,133
[45] Date of Patent: Nov. 5, 1996

[54] PENETRATING INSTRUMENT WITH SEQUENTIAL INDICATION OF ENTRY INTO ANATOMICAL CAVITIES

[76] Inventor: InBae Yoon, 2101 Highland Ridge Dr., Phoenix, Md. 21131

[21] Appl. No.: 457,527

[22] Filed: Jun. 1, 1995

[51] Int. Cl.⁶ ............................................. A61B 17/34
[52] U.S. Cl. ........................... 606/185; 604/164; 604/264
[58] Field of Search ............................ 606/185; 604/264, 604/164

[56] References Cited

U.S. PATENT DOCUMENTS

| | | | |
|---|---|---|---|
| 4,186,750 | 2/1980 | Patel | 128/748 |
| 4,215,699 | 8/1980 | Patel | 128/748 |
| 4,299,230 | 11/1981 | Kubota | 128/630 |
| 4,356,826 | 11/1982 | Kubota | 128/630 |
| 4,535,773 | 8/1985 | Yoon | 604/51 |
| 5,226,426 | 7/1993 | Yoon | 604/169 X |
| 5,275,583 | 1/1994 | Crainich | 604/167 |
| 5,292,310 | 3/1994 | Yoon | 604/158 |
| 5,336,176 | 8/1994 | Yoon | 604/164 X |
| 5,336,206 | 8/1994 | Shichman | 604/283 |
| 5,352,206 | 10/1994 | Cushieri et al. | 604/164 |
| 5,385,572 | 1/1995 | Nobles et al. | 606/185 |
| 5,401,247 | 3/1995 | Yoon | 604/165 |
| 5,445,142 | 8/1995 | Hassler, Jr. | 604/164 |
| 5,454,791 | 10/1995 | Tovey et al. | 604/164 |

FOREIGN PATENT DOCUMENTS

| | | | |
|---|---|---|---|
| 94/27513 | 12/1994 | WIPO | 604/167 |

*Primary Examiner*—Michael Powell Buiz
*Assistant Examiner*—Patrick W. Rasche

[57] ABSTRACT

A penetrating instrument for penetrating an anatomical cavity wall to gain access to the anatomical cavity includes a penetrating member having a distal end for penetrating the anatomical cavity wall, a plurality of probes disposed in the penetrating member, and an indicating mechanism operatively associated with the probes for displaying a sequence of sensible signals in response to movement of the probes during penetration of the anatomical cavity wall. Each of the probes has a distal end movable relative to the penetrating member between an extended position where the distal end of the probe protrudes from the distal end of the penetrating member and a retracted position where the distal end of the probe recedes into the penetrating member. In the retracted positions, respective distal ends of the probes are at axially spaced locations along the distal end of the penetrating member such that movement of the probes from the extended positions to the retracted positions occurs sequentially in response to penetration of the anatomical cavity wall by the penetrating member, and movement of the probes from the retracted positions to the extended positions occurs sequentially in response to penetration into the anatomical cavity by the penetrating member.

24 Claims, 8 Drawing Sheets

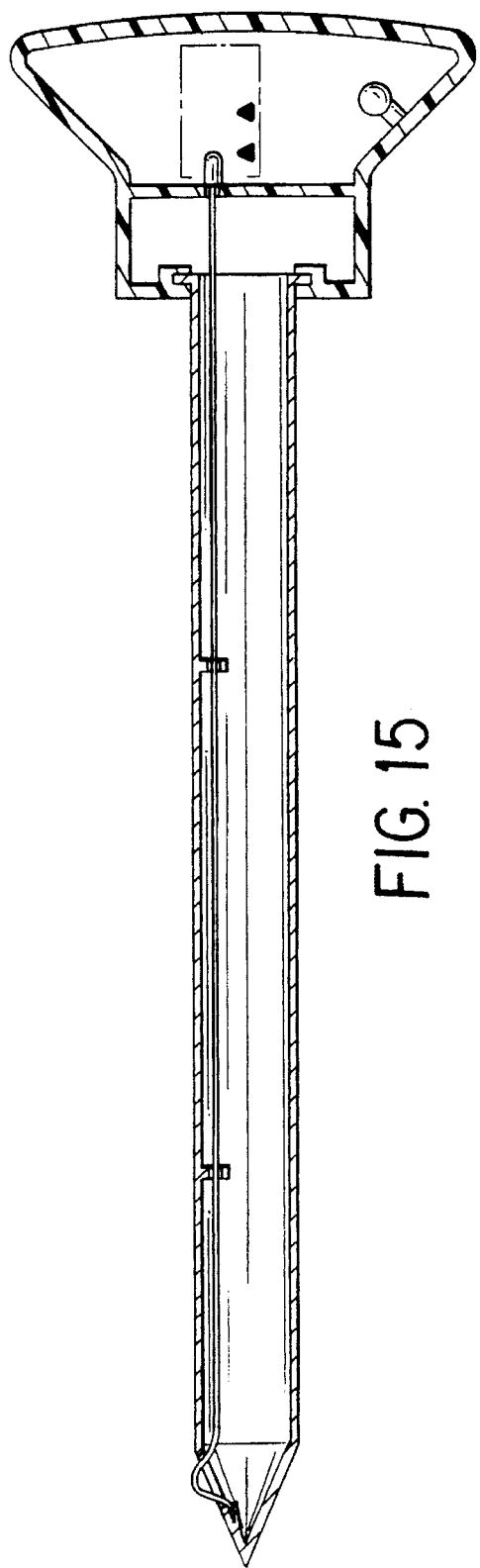
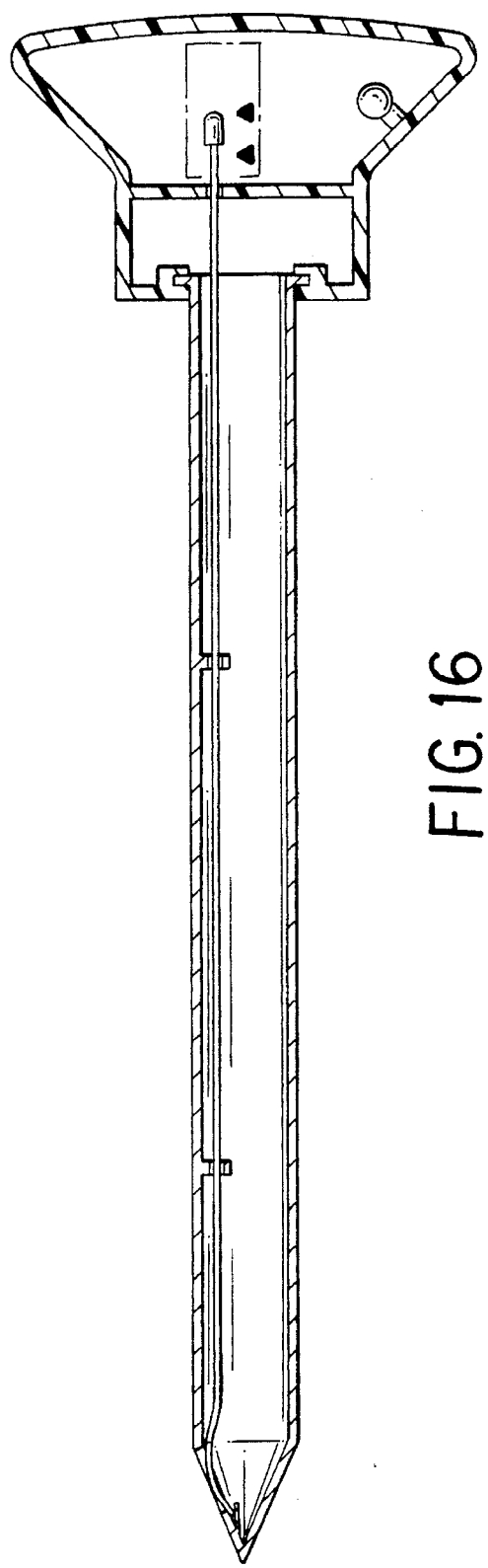

PENETRATING INSTRUMENT WITH SEQUENTIAL INDICATION OF ENTRY INTO ANATOMICAL CAVITIES

BACKGROUND OF THE INVENTION

1. Field of the Invention

The present invention pertains to penetrating instruments for penetrating walls of anatomical cavities and, more particularly, to penetrating instruments having mechanisms for indicating entry of the penetrating instruments into the anatomical cavities.

2. Discussion of the Prior Art

Penetrating instruments are widely used in medical procedures to gain access to anatomical cavities ranging in size from the abdomen to small blood vessels, such as veins and arteries, epidural, pleural and subarachnoid spaces, heart ventricles and spinal and synovial cavities. Use of penetrating instruments has become an extremely popular and important first step in endoscopic, or minimally invasive, surgery to establish an endoscopic portal for many various procedures, such as laparoscopic procedures in the abdominal cavity. Such penetrating instruments typically include a cannula or portal sleeve and a penetrating member, such as a trocar, disposed within the cannula and having a sharp tip for penetrating an anatomical cavity wall with the force required to penetrate the cavity wall being dependent upon the type and thickness of the tissue forming the cavity wall. Once the wall is penetrated, it is desirable to protect tissue or organ structures in forming the cavity from inadvertent contact with the sharp tip of the penetrating member in that, once penetration is achieved, the lack of tissue resistance can result in the sharp tip traveling too far into the cavity and injuring adjacent tissue or organ structures.

A disadvantage of many prior art penetrating instruments is that they do not provide surgeons with an incremental or progressive indication of entry into the anatomical cavity during the penetrating procedure. As a result, surgeons have been forced to estimate when the sharp tip of the penetrating instrument has penetrated through the anatomical cavity wall and how far the tip protrudes into the cavity in order to determine when to reduce or remove the force applied to the penetrating instrument during penetration. In the case of small cavities, in particular, slight errors in estimating the progress of entry into an anatomical cavity can lead to the sharp tip of the penetrating member traveling too far into the cavity causing severe complications.

The penetrating instruments described in U.S. Pat. Nos. 4,186,750; 4,215,699; and 5,352,206 are representative of prior art penetrating instruments that make use of ports to communicate fluid pressure within an anatomical cavity to indicating devices, such as whistles or membranes, located at the proximal ends of the penetrating instruments. Unfortunately, penetrating instruments of this type merely confirm the presence of a penetrating member within an anatomical cavity and cannot provide a progressive indication of entry into the anatomical cavity during the penetrating procedure.

Other penetrating instruments employ complicated arrays of pressure sensors or transducers to provide an indication of the progress of an instrument during the process of penetrating an anatomical cavity wall. These include U.S. Pat. Nos. 4,299,230; 4,356,826; and 4,535,373.

SUMMARY OF THE INVENTION

Accordingly, it is a primary object of the present invention to improve penetrating instruments of the type that provide an indication of entry into an anatomical cavity.

It is another object of the present invention to utilize mechanical movement of probes disposed in the penetrating member of a penetrating instrument to provide visual, audible and/or tactile signals indicative of the progress of entry into an anatomical cavity.

Some of the advantages of the present invention over the prior art are that the progress of entry into an anatomical cavity can be determined without the need of having to introduce electrical components into the surgical field, that a combination of audible, visual and tactile signals indicative of the progress of entry into an anatomical cavity can be generated simultaneously without the need for complicated electronics, and that the penetrating instruments of the present invention can be inexpensively manufactured with minimum components to reduce costs, facilitate sterilization for reuse and allow economical, single patient use.

The present invention is generally characterized in a penetrating instrument for penetrating an anatomical cavity wall to gain access to the anatomical cavity including a penetrating member having a distal end for penetrating the anatomical cavity wall, a plurality of probes disposed in the penetrating member, each of the probes having a distal end movable relative to the penetrating member between an extended position where the distal end of the probe protrudes from the distal end of the penetrating member and a retracted position where the distal end of the probe recedes into the penetrating member, means for biasing the probes toward their respective extended positions, and indicating means operatively associated with the probes for displaying a sequence of sensible signals in response to movement of the probes during penetration of the anatomical cavity wall. In their respective extended positions, the probes protrude from axially spaced locations at the distal end of the penetrating member such that during penetration of the anatomical cavity wall, the force from tissue contact with the probes causes the probes to move sequentially from their respective extended positions to their respective retracted positions against the bias of the biasing means. When the distal end of the penetrating member penetrates into the anatomical cavity, the reduction in force from tissue contact permits the bias means to move the probes sequentially from their respective retracted positions to their respective extended positions.

Another aspect of the present invention is generally characterized in a method of forming a portal in the wall of an anatomical cavity including the steps of penetrating the anatomical cavity wall with a penetrating member of a penetrating instrument having a plurality of probes protruding from a distal end of the penetrating member at axially spaced locations, biasing each probe to an extended position where a distal end of the probe protrudes outwardly of the penetrating member distal end, permitting the probes to move sequentially from extended positions protruding outwardly of the penetrating member distal end to retracted positions within the penetrating member in response to penetration of the anatomical cavity wall by the penetrating member, and indicating progress of entry into the anatomical cavity by displaying a sequence of sensible signals in response to movement of the probes during penetration of the anatomical cavity wall. In one embodiment, the indicating step includes displaying movement of the proximal ends of the probes. The movement of the proximal ends of the probes can be viewed through a window formed in a hub of the penetrating instrument. Penetration of the anatomical cavity wall can be suspended when one or more of the probes is observed to have moved from the retracted position to the extended position in response to a reduction in force from tissue contact, at which time a cannula can be advanced distally along the penetrating member to be placed within the anatomical cavity wall.

Other objects and advantages of the present invention will become apparent from the following description of the preferred embodiments taken in conjunction with the accompanying drawings wherein, unless otherwise specified, like parts in each of the several figures are identified by the same reference numerals or by reference numerals sharing the same last two digits.

BRIEF DESCRIPTION OF THE DRAWINGS

FIG. 15 is a top view, in section, showing another modification of the penetrating instrument according to the present invention.

FIG. 16 is a top view, in section, illustrating operation of the penetrating instrument of FIG. 15.

DESCRIPTION OF THE PREFERRED EMBODIMENTS

The penetrating instrument of the present invention is described hereinafter for use as an instrument for inserting a portal sleeve through a wall of an anatomical cavity to form a portal for the introduction of various surgical and diagnostic instruments into the cavity during endoscopic procedures, such as laparoscopy. It is understood, however, that the penetrating instrument of the present invention can be used for penetration or introduction into anatomical cavities of needles with fluid flow therethrough and catheters as well as for other instruments engaging tissue during surgical or diagnostic procedures. Accordingly, the cannula or outer tubular member of the safety penetrating instrument can be a portal sleeve, a needle, a catheter or a tubular component of a medical instrument.

Figure 1:
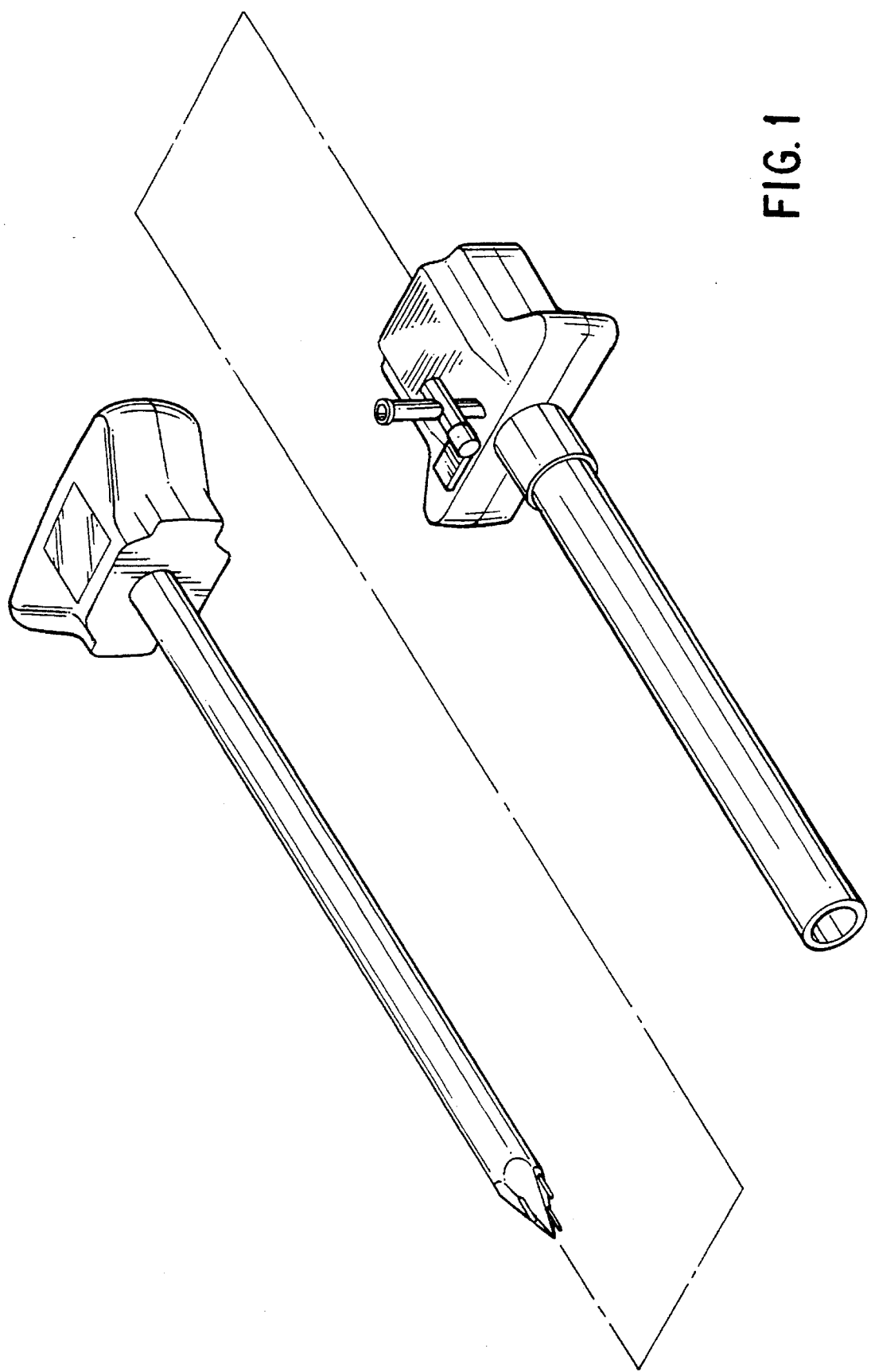
FIG. 1 is an exploded perspective view of a penetrating instrument according to the present invention.
Figure 2:
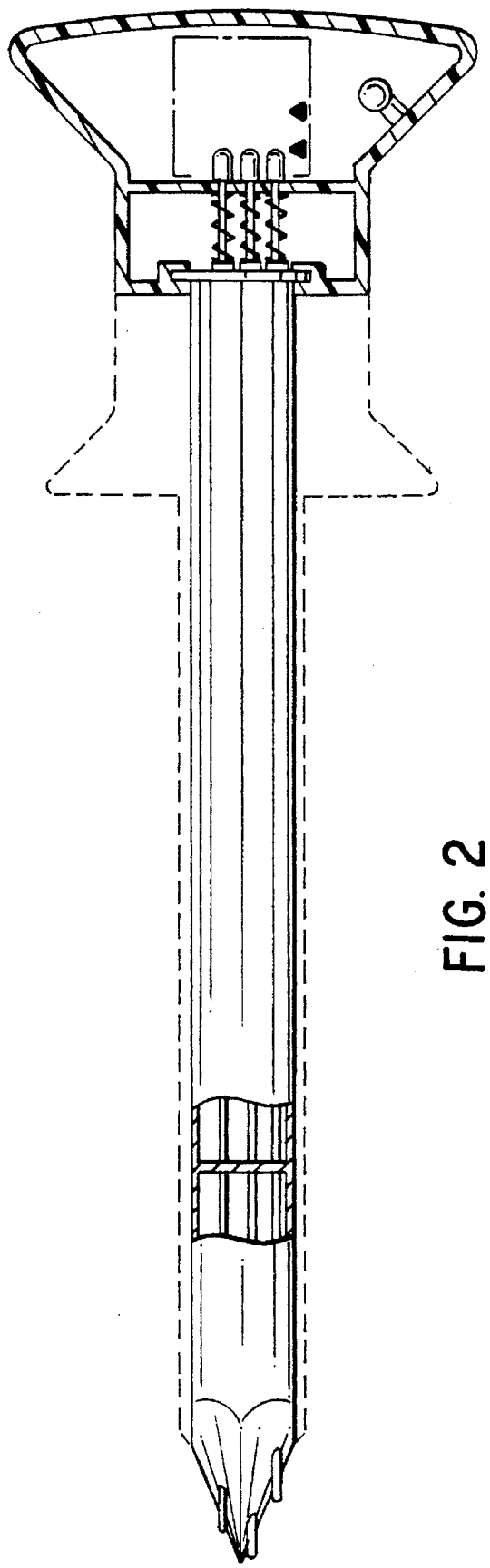
FIG. 2 is a top plan view, partly in section, of the penetrating instrument of FIG. 1.

A penetrating instrument 20 according to the present invention, as shown in FIGS. 1 and 2, is formed of a portal unit 22 and a penetrating unit 24. The portal unit 22 includes an elongate portal sleeve, cannula or catheter 26 and a housing 28 mounted at a proximal end 30 of the portal sleeve. Portal sleeve 26 and housing 28 of the portal unit can be made of any desirable medically acceptable materials depending on procedural use and desirability of being for single patient use or reusable and can be of integral one-piece construction as shown or formed separately and joined together. Portal sleeve 26 is preferably cylindrical or tubular in configuration to define a lumen for receiving a penetrating member 32 of the penetrating unit. Proximal end 30 of the portal sleeve is secured to a front wall 34 of housing 28.

Housing 28 of the portal unit is preferably constructed to sealingly engage instruments passing therethrough and to include a valve (not shown) biased to a closed state when no instrument passes through the portal sleeve. Any suitable valve construction can be utilized including, for example, flapper, trumpet or nipple valves. Housing 28 can have any desirable configuration in cross-section to facilitate grasping by the surgeon and can have various valves, stopcocks and seals to control fluid flow therethrough as well as various adapters to adjust to the size of instruments inserted through the portal unit.

Penetrating unit 24 includes penetrating member 32, a plurality of sensors or probes 38a, 38b and 38c disposed in the penetrating member and a hub 40 mounting a proximal end of the penetrating member. Penetrating member 32 includes a round disk-like cap or flange 42 at a proximal end, a sharp distal end 44 and a hollow tubular body 46 extending between the proximal and distal ends. An interior wall or support 47 extends across the tubular body of the penetrating member and is formed with openings to permit passage of the probes through the interior wall. The penetrating member distal end 44 includes a plurality of beveled surfaces or facets 48a, 48b and 48c extending from a shoulder or junction 50 to define a sharp, tissue penetrating tip 52. Distal end 44 can have any configuration desired by a surgeon for a particular procedure including, for example, the solid pyramidal trocar configuration shown or conical, threaded, multifaceted or open, slanted or needle configurations.

Hub 40 can have any desired external configuration to facilitate grasping of the portal unit and the penetrating unit by the surgeon with one hand. As best seen in FIG. 2, hub 40 includes front and rear walls 56 and 58 oriented perpendicular or substantially perpendicular to a longitudinal axis of the penetrating instrument and a pair of spaced sidewalls 60 and 62 extending between the front and rear walls of the housing on opposite sides of the instrument longitudinal axis. An inner wall or partition 64 extends transversely between sidewalls 60 and 62 in configuration parallel to front wall 56 and is disposed between front and rear walls of the housing. Penetrating member 32 extends through an opening in the front wall 56 of the hub to terminate proximally at flange 42 which is held stationary within a slot, pocket or clip 65 formed on an inner surface or back face of the housing front wall. Referring again to FIG. 1, a translucent or transparent portion or window 66 is formed in a top wall 68 of the hub 40 between inner and rear walls 64 and 58 to provide visual access to the interior of hub 40; and, as shown in FIG. 2, indicia or markings 70 can be formed opposite the transparent portion or window 66 on a bottom wall 72 of the hub between inner wall or partition 64 and rear wall 58. Indicia 70 are shown as a pair of axially spaced arrowheads but can be any type of marking, coloring or scale against which longitudinal movement of a probe can be easily gauged or noted by visual inspection through window 66.

Probes 38a, 38b and 38c can be made of any medically acceptable rigid or semi-rigid, metal or plastic material and are of essentially the same structure with the exception of overall length. Hereinafter, for purposes of clarity, only one of the probes will be described in detail, it being understood that the other probes are of similar structure to that described as indicated by the use of identical reference numerals followed by an appropriate letter suffix identifying the corresponding probe. Referring now to probe 38a in FIG. 2, it can be seen that the probe has a rod-like configuration with a distal end or tip 74a extending through an aperture formed at the penetrating member distal end 44. Tip 74a can be rounded as shown or have any other configuration desired including, for example, flat or beveled configurations wherein the tip is flush with the beveled distal end of the penetrating member when in a retracted position as will be described more fully below. The probe extends longitudinally through axially aligned openings formed in the interior wall 47 and flange 42 of the penetrating member and the hub inner wall 64 to terminate proximally at an enlarged head or button 76a disposed between the inner wall 64 and rear wall 58 of the hub. Button 76a can be of any shape or size and color to be noticed by the surgeon but is preferably cylindrical with a rounded proximal end as shown and with a color contrasting with that of the walls of the hub 40. A flange 78a is formed or carried by the probe 38a and is distally spaced from the button 76a to be disposed between the penetrating member flange 42 and the hub inner wall 64. A bias member 80a acts on the flange 42 to bias the probe 38a in a distal direction toward an extended position where the distal tip 74a of the probe protrudes beyond the beveled face or surface 48a of the penetrating member distal end 44, flange 78a of the probe abuts the penetrating member flange 42 and button 76a is aligned with the distalmost arrowhead or scale marking of indicia 70. Bias member 80a is shown as a helical coil spring held in compression between flange 78a of the probe and the hub inner wall 64; however, any type of spring or bias device can be used including, for example, tension springs, compression springs, torsion springs, pan springs, pivotally connected members, rubber, plastic, or magnets.

Figure 3:
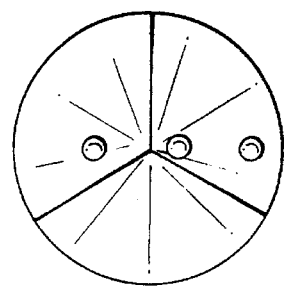
FIG. 3 is a frontal view in elevation of the penetrating instrument of FIG. 1.

Probes 38a, 38b and 38c extend in parallel through penetrating member 32 in diametrically spaced relation. In their respective extended positions, buttons 76a, 76b and 76c are held in axial alignment against hub inner wall 64; however, as best seen in FIG. 3, distal tip 74a of probe 38a protrudes from an aperture formed in beveled face 48a of the penetrating member adjacent the sharp, tissue penetrating tip 52 while the distal tip 74b of probe 38b is proximally spaced from distal tip 74a, and the distal tip 74c of probe 38c is proximally spaced from distal tip 74b. Probe 38b is shorter than probe 38a and is disposed opposite probe 38a on the other side of the central longitudinal axis or tip 52 of the penetrating instrument such that, in the extended position, the distal tip 74b of probe 38b protrudes from an aperture formed in beveled face 48b. Probe 38c is shorter than probe 38b and is disposed opposite probe 38b on the other side of probe 38a so as to protrude from another aperture formed at a radially and axially spaced location on beveled face 48a.

A bulb or other lighting device 81 can be located within the hub 40 adjacent window 66 to illuminate buttons 76a, 76b and 76c and indicia 70. The bulb can be powered externally by power cord or internally by battery and can be manually or automatically operated.

The portal unit 22 and the penetrating unit 24 can be provided to a surgeon separately or assembled together, and either or both of the portal and penetrating units can be manufactured in a manner to be disposable for single patient use or to be sterilizable for reuse. The hub 40 can be coupled to the housing 28 by any suitable detent or latch mechanisms if desired, and the penetrating unit 24 can be withdrawn from the portal unit 22 leaving the portal sleeve 26 in place within an anatomical cavity.

In use, penetrating instrument 20 will normally be in the assembled condition shown in FIG. 2 where the portal unit 22, shown by broken lines, is coupled with the penetrating unit 24. In the assembled condition, the penetrating member 32 is disposed within the portal sleeve 26, and the distal end 44 of the penetrating member protrudes distally from the portal sleeve distal end 82. Prior to penetrating into an anatomical cavity wall W, probes 38a, 38b and 38c will be in the extended positions shown in FIG. 2 with buttons 76a, 76b and 76c abutting inner wall 64 of hub 40 and being visibly aligned with a distalmost marking or arrowhead of indicia 70.

Figure 4:
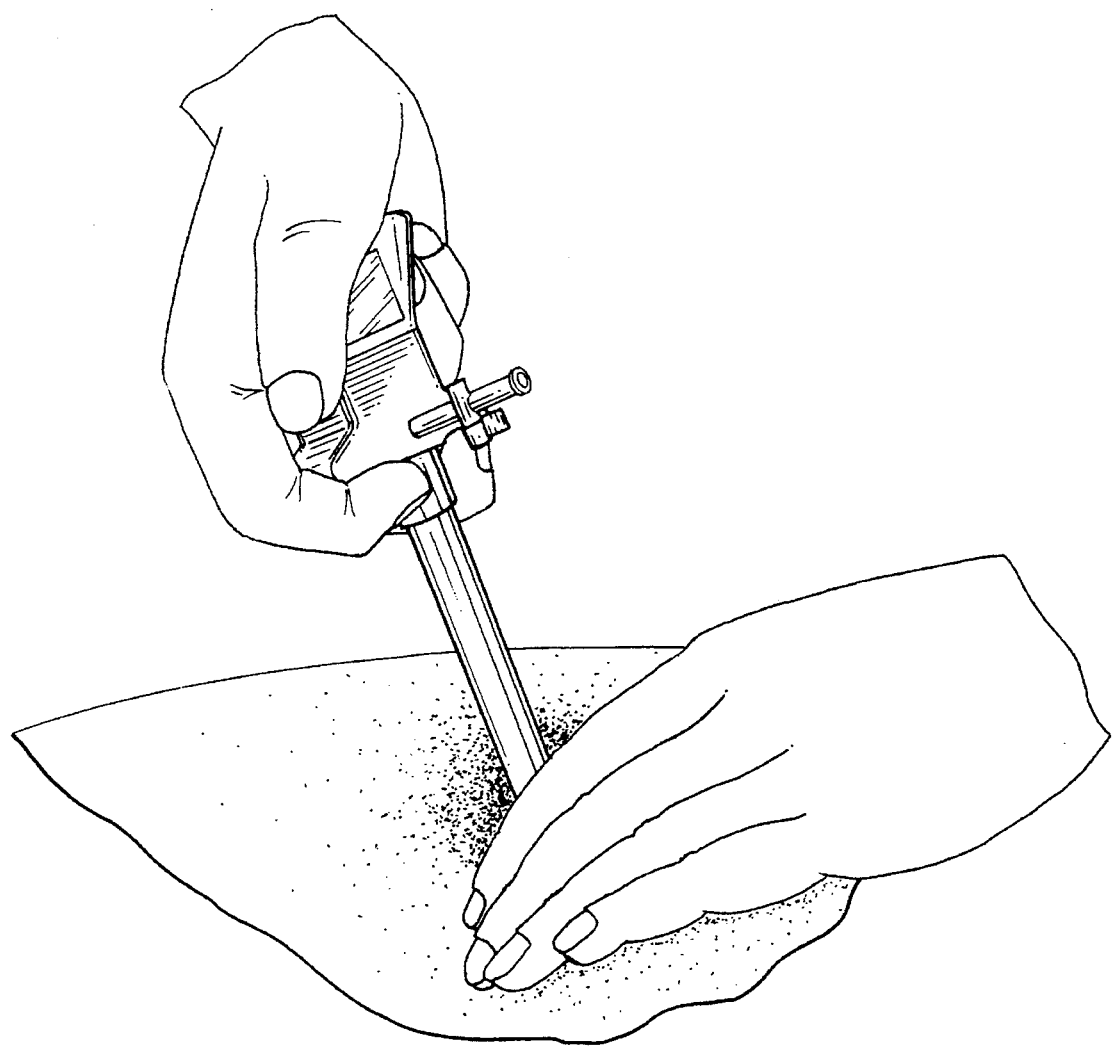
FIG. 4 is a diagrammatic view illustrating use of the penetrating instrument of FIG. 1.
Figure 5:
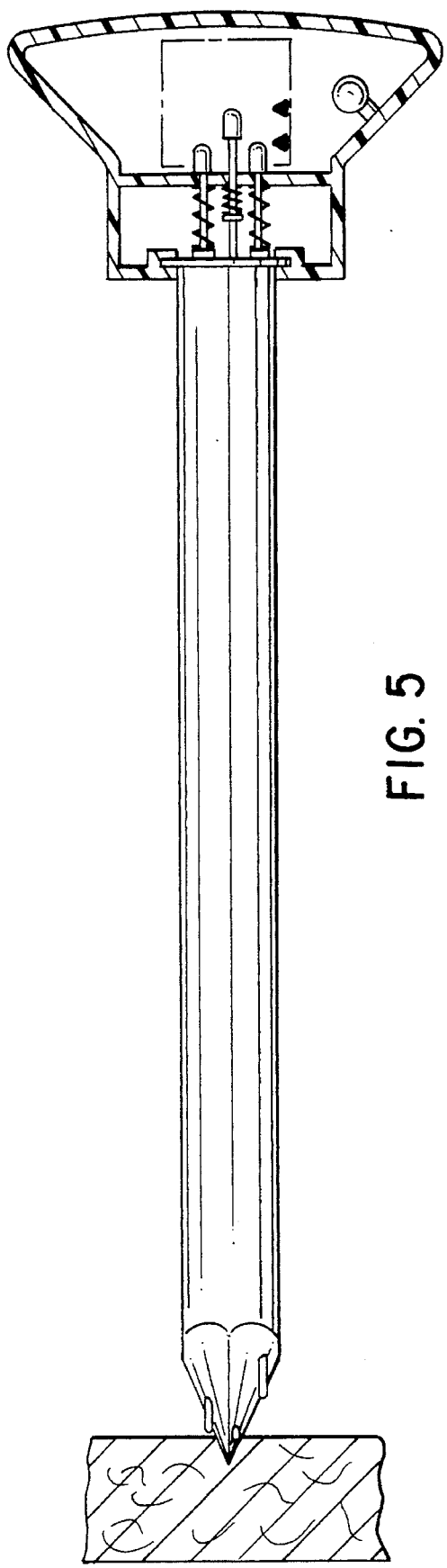
FIGS. 5–8 are top views, partly in section, illustrating use of the penetrating instrument of FIG. 1.

When it is desired to penetrate into the anatomical cavity wall W, the penetrating instrument 20 is preferably grasped using one hand as shown in FIG. 4 with window 66 in the top wall of the hub 40 facing outward from the palm of the grasping hand to be in the field of view of the surgeon during penetration of the anatomical cavity wall W. The sharp tip 52 of the penetrating member 32 is then brought into contact with the tissue forming the anatomical cavity wall W, and a distal force is exerted on the penetrating instrument 20 to advance the sharp tip 52 of the penetrating member into the tissue. Tip 74a of probe 38a is disposed adjacent the sharp tip 52 of the penetrating member and, as shown in FIG. 5, at about the same time that the sharp tip 52 of the penetrating member makes contact with the tissue forming the anatomical cavity wall W, the tip 74a of the probe 38a will also be brought into contact with the wall. The force from tissue contact with the probe tip 74a causes the probe 38a to be moved proximally relative to the penetrating member 32 from the extended position to the retracted position against the influence of bias member 80a during penetration. As a result, distal tip 74a of probe 38a recedes into distal end 44 of the penetrating member, and button 76a at the proximal end of probe 38a is visibly moved proximally beneath window 66 towards a proximal marking or arrowhead of indicia 70 providing a visual signal to the surgeon that the sharp tip 52 of the penetrating instrument has penetrated into the anatomical cavity wall W. So long as the distal tip 74a of the probe 38a is disposed within the anatomical cavity wall, the force from tissue contact with the distal tip will prevent the probe from moving distally from the retracted position to the extended position, and the button 76a will be aligned with the proximal marking or arrowhead of indicia 70.

Figure 6:
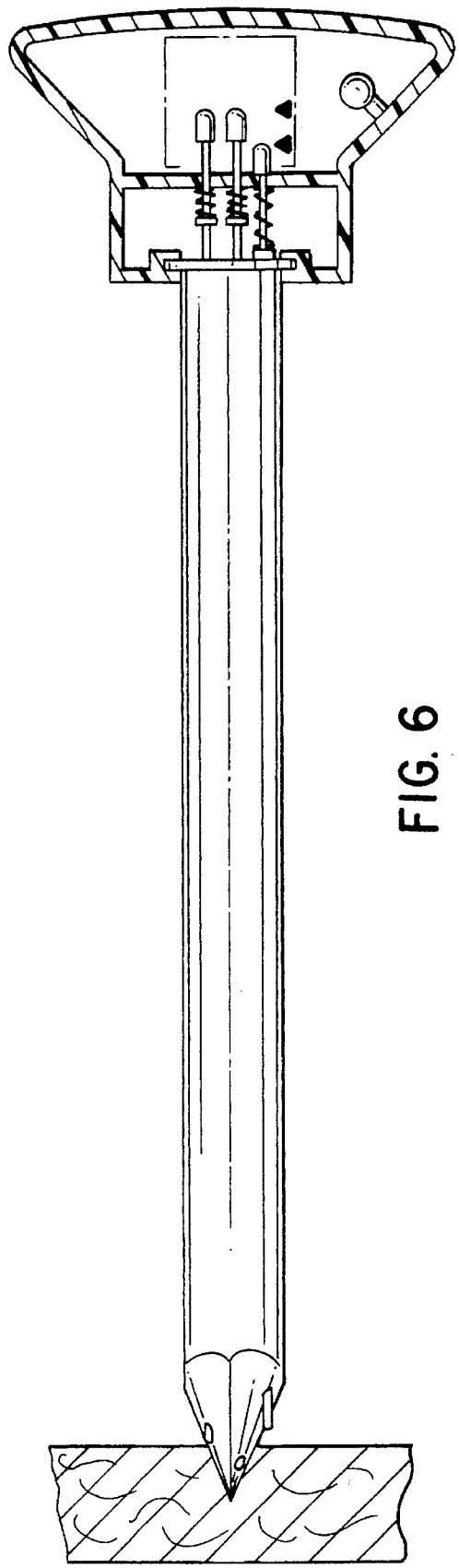

As the distance travelled by the sharp tip 52 of the penetrating member 32 through the anatomical cavity wall W or, in other words, the depth of penetration, increases, distal tip 74b of probe 38b is brought into contact with the tissue forming the anatomical cavity wall W as shown in FIG. 6, and the force from tissue contact with the probe tip 74b causes the probe 38b to be moved proximally relative to the penetrating member 32 from the extended position to the retracted position against the influence of bias member 80b during penetration. As a result, distal tip 74b of probe 38b recedes into distal end 44 of the penetrating member, and button 76b at the proximal end of probe 38b is visibly moved proximally beneath window 66 towards the proximal marking or arrowhead of indicia 70 providing a visual signal to the surgeon that the sharp tip 52 of the penetrating instrument has penetrated into the anatomical cavity wall W an axial distance corresponding approximately to the distance between the tip 52 and the aperture through which probe 38b extends.

If the anatomical cavity wall W is thicker than the axial spacing between the tips of probes 38a and 38b, the probes will both be in the retracted positions shown in FIG. 6, and buttons 76a and 76b will be axially aligned with the proximal marking or arrowhead of indicia 70. In the event the anatomical cavity wall is thinner than the axial spacing between the tips of probes 38a and 38b, it will be appreciated that sudden distal movement of button 76a from the retracted position to the extended position, even before any of the other probes are moved proximally, will signal a reduction in force from tissue contact caused by penetration of the tip 52 of the penetrating member into the anatomical cavity.

Figure 7:
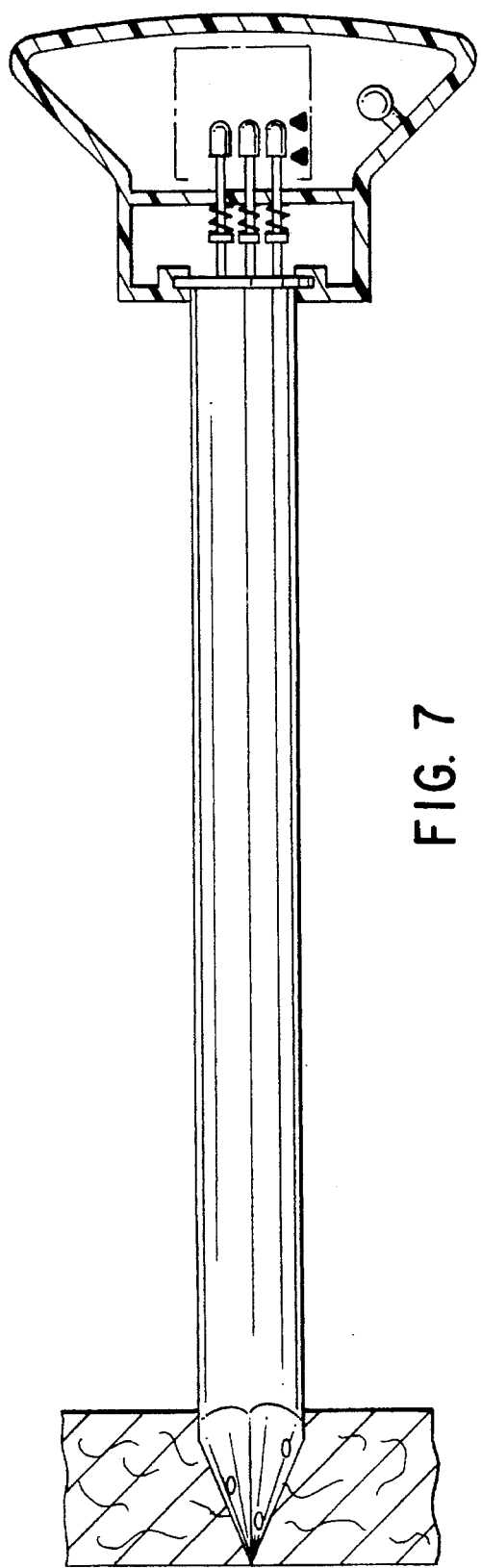

Upon further penetration of the anatomical cavity wall W, distal tip 74c of probe 38c is brought into contact with the tissue forming the anatomical cavity wall W as shown in FIG. 7, and the force from tissue contact with the probe tip 74c causes the probe 38c to be moved proximally relative to the penetrating member 32 from the extended position to the retracted position against the influence of bias member 80c during penetration. As a result, distal tip 74c of probe 38c recedes into distal end 44 of the penetrating member, and button 76c at the proximal end of probe 38c is visibly moved proximally beneath window 66 towards the proximal marking or arrowhead of indicia 70 providing a visual signal to the surgeon that the sharp tip 52 of the penetrating member has penetrated into the anatomical cavity wall W an axial distance corresponding approximately to the distance between the tip 52 and the aperture through which probe 38c extends. If the anatomical cavity wall W is thicker than the axial spacing between the tips of probes 38a and 38c, all of the probes 38a, 38b and 38c will now be in the retracted positions shown in FIG. 7, and buttons 76a, 76b and 76c will be axially aligned with the proximal marking or arrowhead of indicia 70.

Figure 8:
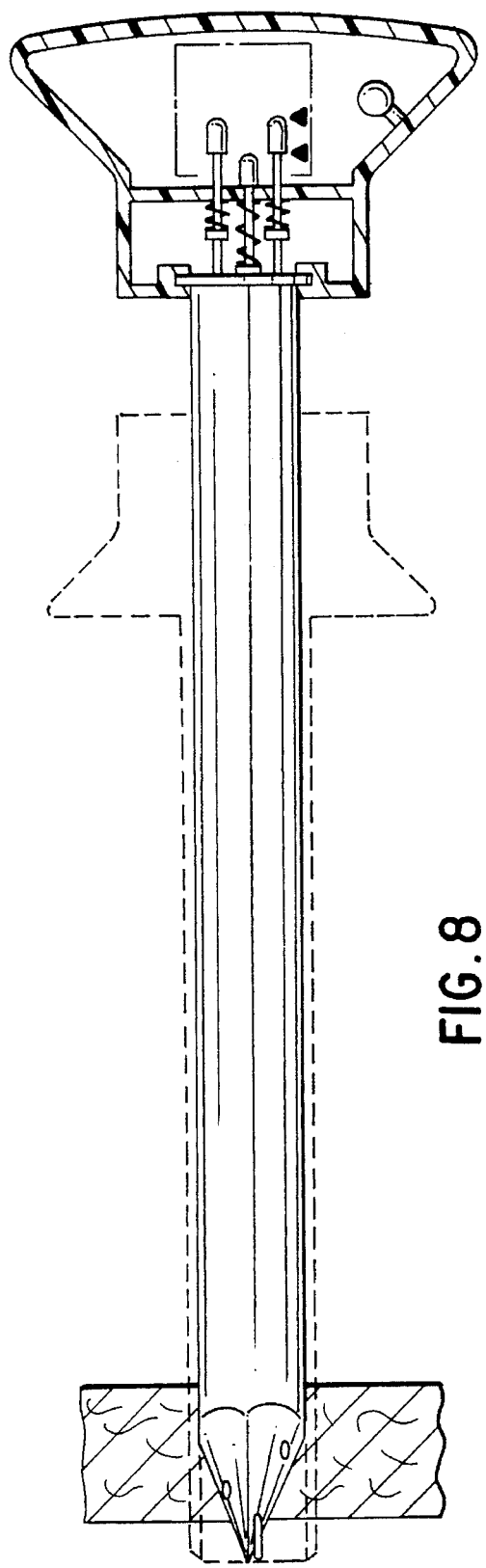
Figure 9:
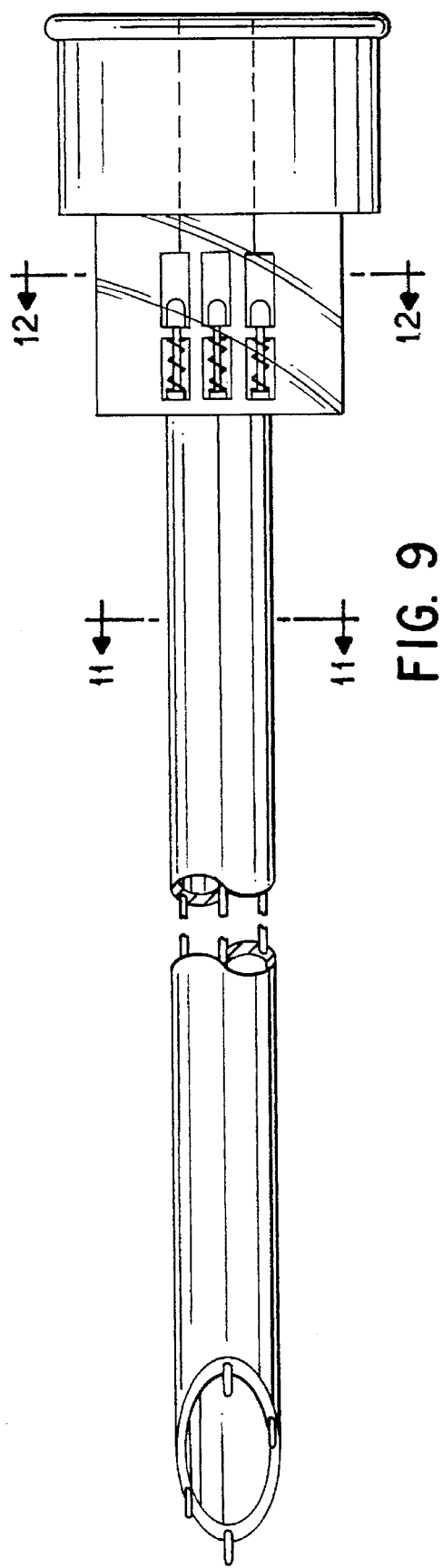
FIG. 9 is a top plan view, in broken longitudinal section, showing a modified penetrating instrument according to the present invention.
Figure 10:
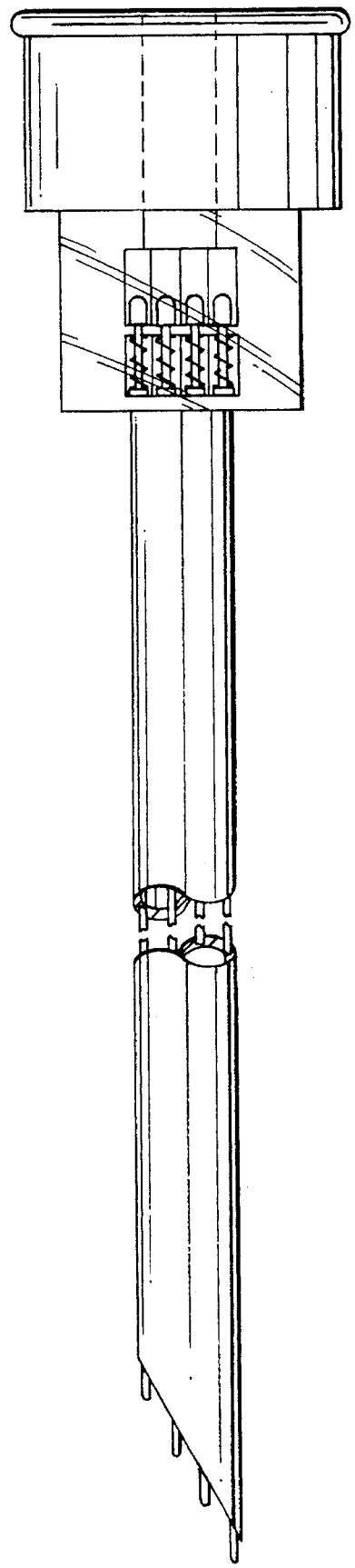
FIG. 10 is a side elevational view, in broken longitudinal section, of the penetrating instrument of FIG. 9.
Figure 11:
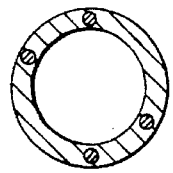
FIG. 11 is a cross-sectional view of the penetrating instrument of FIG. 9 taken through line 11—11.
Figure 12:
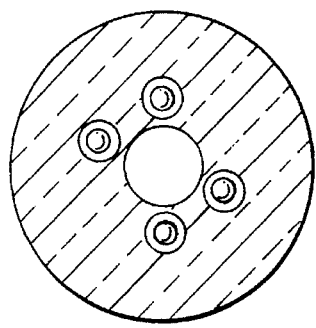
FIG. 12 is a cross-sectional view of the penetrating instrument of FIG. 9 taken through line 12—12.

When the sharp, tissue penetrating tip 52 of the penetrating member 32 penetrates through the anatomical cavity wall W as shown in FIG. 8, the force from tissue contact with the distal tip 74a of probe 38a is reduced or removed permitting bias member 80a to move the probe distally relative to the penetrating member from the retracted position to the extended position. Tip 74a will thus protrude distally from the penetrating member distal end 44 and button 76a at the proximal end of the probe 38a will be made to abut inner wall 64 of the hub providing a visible indication of penetration of the anatomical cavity wall by the sharp tip 52 of the penetrating member. Impact of button 76a with inner wall 64 of the hub can also generate an audible click and/or tactile signal that can be sensed by the surgeon as a further indication of penetration into the anatomical cavity.

At this point, the force exerted upon the penetrating instrument 20 can be reduced as needed to protect anatomical tissue and organs in or forming the anatomical cavity from the sharp tip 52 of the penetrating member. If the anatomical cavity is particularly small, such that penetration of the anatomical cavity wall by the entire length of the penetrating member distal end 44 is to be avoided, movement of probe 38a from the retracted position to the extended position can serve as a signal to the surgeon to stop penetration, at which time the portal unit 22 can be advanced distally along the penetrating member 32 and into the anatomical cavity as shown by broken lines in FIG. 8. In cases where it is desirable for more than the sharp tip 52 of the penetrating member distal end to protrude or penetrate into the anatomical cavity, such as when tissue or fluid samples are to be collected from the anatomical cavity via a lumen formed through the penetrating member, penetration of the anatomical cavity wall W can be continued while monitoring the position of buttons 76b and 76c at the proximal ends of probes 38b and 38c. When the tip 74b of probe 38b penetrates through the anatomical cavity wall W, the force from tissue contact with distal tip 74b of probe 38b is reduced or removed permitting bias member 80b to move probe 38b distally relative to the penetrating member from the retracted position to the extended position. Distal movement of probe 38b is limited by impact of button 76b at the proximal end of the probe with the inner wall 64 of the hub, which serves as a stop or abutment preventing further distal movement of the probe. Movement of button 76b distally beneath window 66 towards the inner wall 64, along with any audible or tactile signal generated by the impact of button 76b with the inner wall, serve as indications to the surgeon that the sharp tip 52 of the penetrating member has penetrated into the anatomical cavity an axial distance corresponding approximately to the distance between the tip 52 and the aperture through which probe 38b extends.

Upon further penetration into the anatomical cavity, the distal tip 74c of probe 38c will penetrate through the anatomical cavity wall W into the anatomical cavity, and the force from tissue contact with the distal tip 74c will be reduced or removed permitting bias member 80c to move the probe distally relative to the penetrating member from the retracted position to the extended position. Distal movement of button 76c at the proximal end of probe 38c towards inner wall 64 provides a visual, audible and/or tactile signal to the surgeon that the sharp tip 52 of the penetrating member has penetrated into the anatomical cavity an axial distance corresponding approximately to the distance between the tip 52 and the aperture through which probe 38c extends. If the aperture through which probe 38c extends is adjacent junction 50, distal movement of probe 38c will indicate that the entire length of the penetrating member distal end 44 is disposed within the anatomical cavity; and, at that time, penetration can be stopped and the portal unit 22 can be advanced distally along the penetrating member 32 and into the anatomical cavity.

When the distal end 82 of the portal sleeve 26 is disposed within the anatomical cavity, the penetrating unit 24 including the penetrating member 32 can be withdrawn from the portal unit 22 leaving the portal sleeve in place to form a portal for introducing instruments into the anatomical cavity.

The penetrating member of the penetrating instrument according to the present invention can have any configuration desired by a surgeon for a particular procedure including, for example, the solid pyramidal trocar configuration shown or conical, threaded, multifaceted, beveled or blunt configurations. In FIGS. 9–12, a modification of the penetrating unit is shown wherein the penetrating member is configured as a needle 132. Needle 132 of the modified penetrating unit 124 includes a hollow shaft or body 146 defining a lumen 133 between proximal and distal ends 142 and 144 of the needle. Shaft 146 is preferably cylindrical or tubular in cross-section with a wall thickness t chosen to maintain a sharp edge and to provide suitable rigidity for penetrating anatomical tissue. Distal end 144 of the needle is beveled to define a sharp, tissue penetrating tip 152 but can have other configurations depending upon procedural use. Proximal end 142 of the needle mounts a hub 140 having a cylindrical front portion 166 made of a transparent or translucent material and a rear portion 158 with a configuration to mate with fluid conveying tubes. For example, rear portion 158 of the hub could be configured to form a Luer-type lock. A passage or bore 135 is formed through the hub in axial alignment with lumen 133 to permit fluid flow through the penetrating unit.

A plurality of probes 138a, 138b, 138c and 138d are disposed within longitudinal passages or channels 137 formed in the wall of the needle 132. Probes 138a, 138b, 138c and 138d are similar to those described above but with a lateral dimension or diameter less than the wall thickness t of the needle. Distal ends or tips 174a, 174b, 174c and 174d of the probes protrude from the distal end 144 of the needle in their respective extended positions and are receded into the wall of the needle in their respective retracted positions. The probes terminate proximally at buttons 176a, 176b, 176c and 176d disposed within cylindrical pockets 139 formed in the translucent or transparent portion 166 of hub 140 in axial alignment with channels 137 formed in needle 132. Flanges 178a, 178b, 178c and 178d are carried or formed on probes 138a, 138b, 138c and 138d, respectively, and are disposed within cylindrical pockets 141 formed in hub 140 in axial alignment with and distally spaced from pockets 139. Bias members 180a, 180b, 180c and 180d are mounted between flanges 178a, 178b, 178c and 178d and the proximal end walls of pockets 141 to bias the probes distally toward their respective extended positions.

Use of the modified penetrating unit 124 is essentially the same as described above for penetrating unit 24 with the exception that buttons 176a, 176b, 176c and 176d can be viewed from a number of angles through the translucent or transparent portion 166 of hub 140 to permit greater freedom in grasping the penetrating unit. It will also be appreciated that by use of four probes, the modified penetrating unit 124 permits four increments of penetration into an anatomical cavity to be progressively or sequentially indicated.

Figure 13:
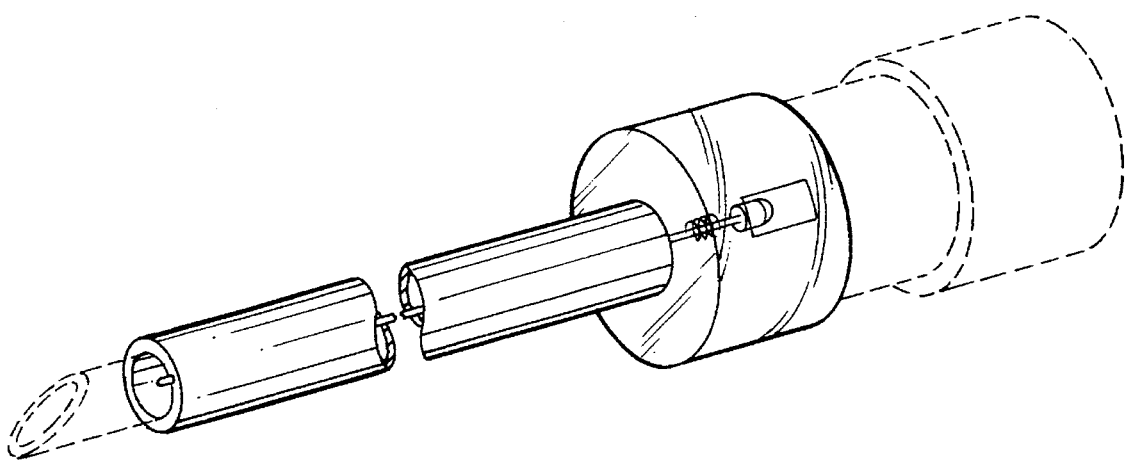
FIG. 13 is a perspective view, in broken longitudinal section, showing a cannula for use with the penetrating instrument of the present invention.

The penetrating unit 124 described above can be coupled with a portal unit, like portal unit 22 shown in FIG. 1, to place a cannula, catheter or portal sleeve in the wall of an anatomical cavity. Another portal unit that can be used with the penetrating unit 124 is shown in FIG. 13 at 122. The modified portal unit 122 is similar to portal unit 22 but with a translucent or transparent housing 128 mounting the proximal end of a catheter 126 and a probe 143 disposed within a tubular wall of the catheter. Portal unit 122 defines a lumen 45 for receiving a penetrating member, such as needle 132 of penetrating unit 124 as shown by broken lines in FIG. 13. Probe 143 is similar to the probes previously described but is used to indicate penetration by the catheter in an anatomical cavity. The probe 143 terminates distally at a distal end or tip 147 that protrudes from the distal end 182 of the catheter and proximally at a head or button 149 disposed within a pocket 151 formed beneath a translucent or transparent portion 153 of the housing 128. A bias member 155 biases the probe 143 distally to the extended position shown while permitting proximal movement of the probe toward a retracted position in response to the force from tissue contact with the tip of the probe during penetration of an anatomical cavity wall. In the retracted position, button 149 is disposed at the proximal end of pocket 151. Upon penetrating into the anatomical cavity, probe 143 is moved distally under the influence of bias member 155 to the extended position causing button 149 to be disposed at the distal end of the pocket 151. When used with a penetrating unit such as penetrating unit 124, movement of the button 149 provides a visual, audible and/or tactile signal to the surgeon indicating that the distal end 182 of the catheter has entered the anatomical cavity.

Figure 14:
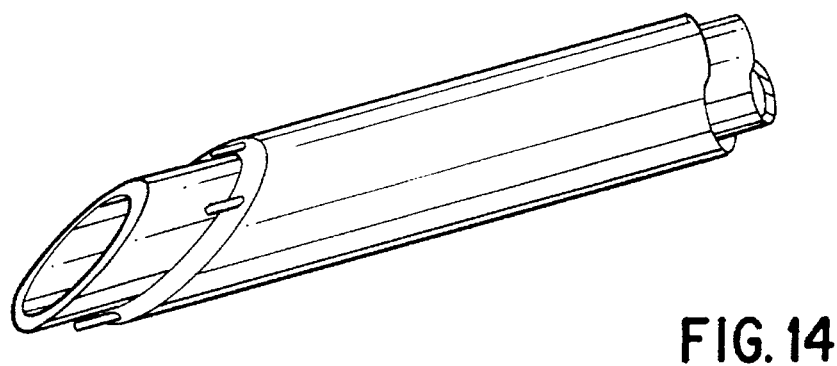
FIG. 14 is a fragmentary perspective view of another cannula for use with the penetrating instrument of the present invention.
Figure 1:
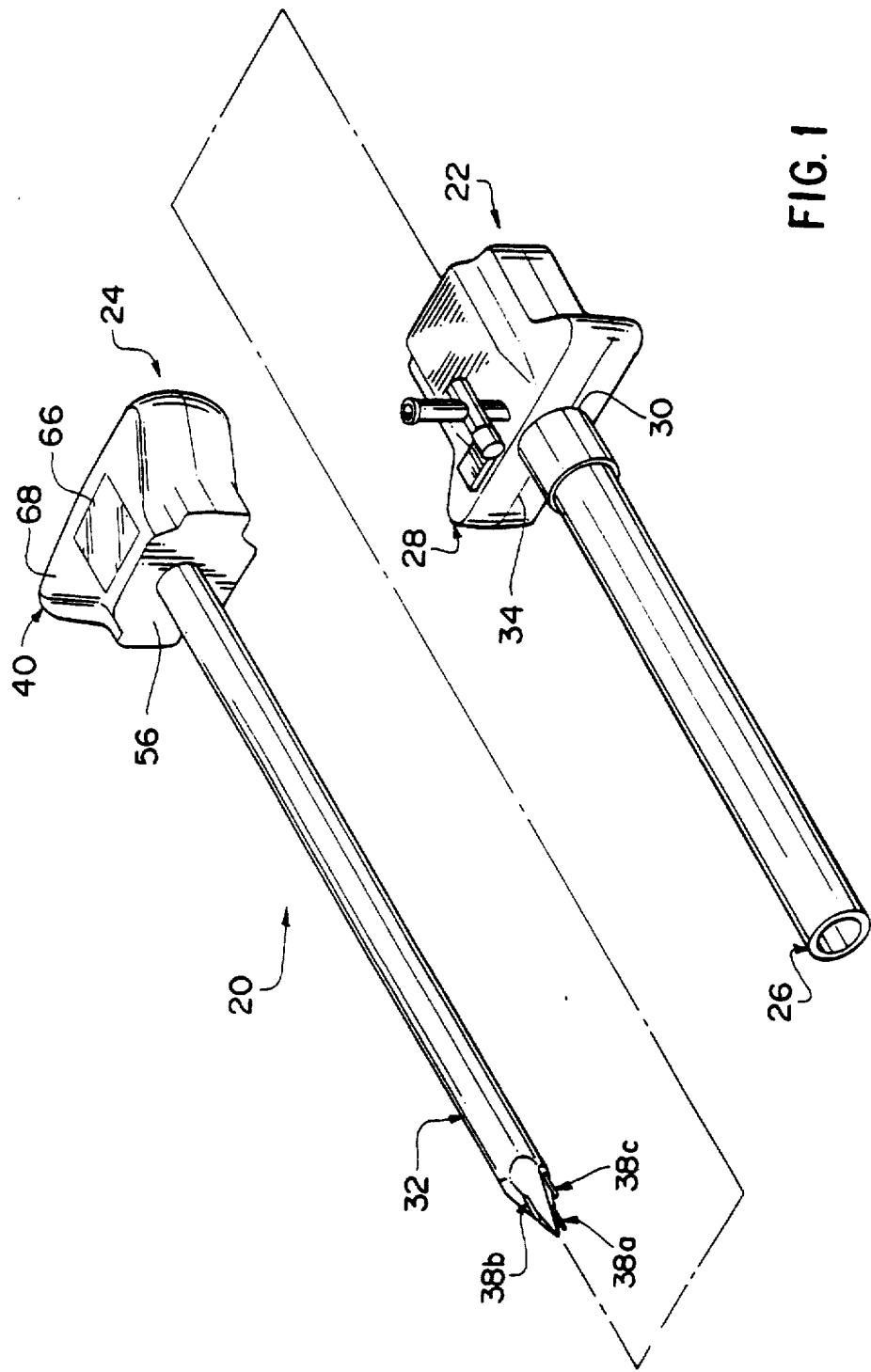
Figure 2:
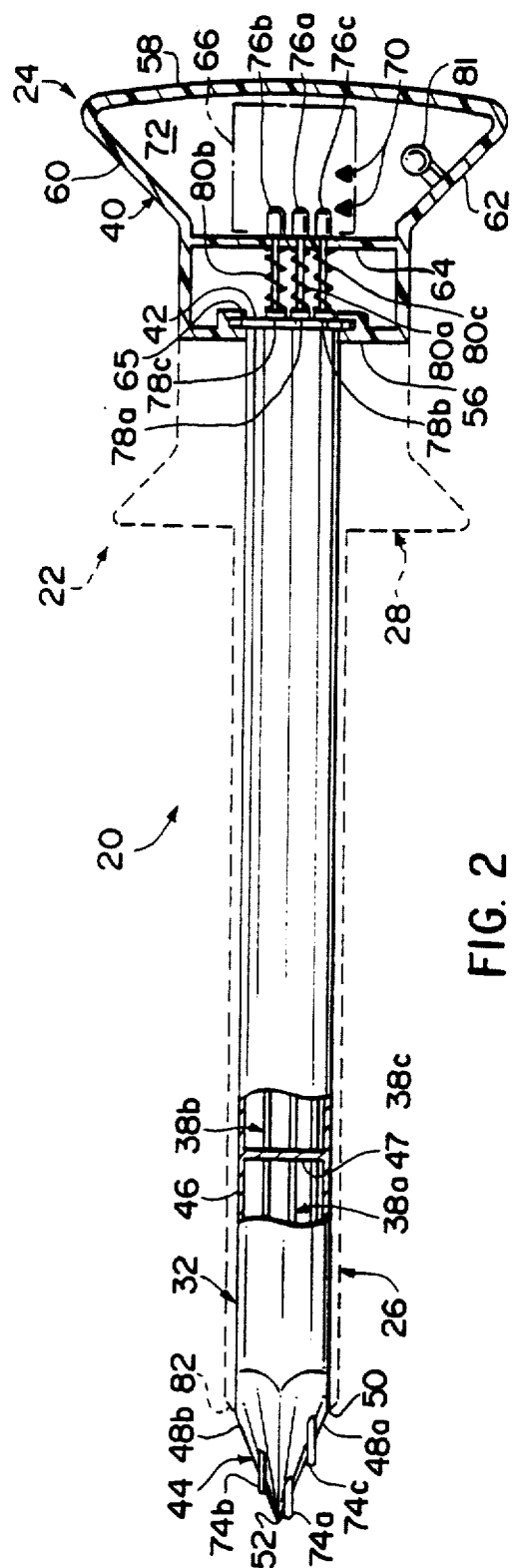
Figure 3:
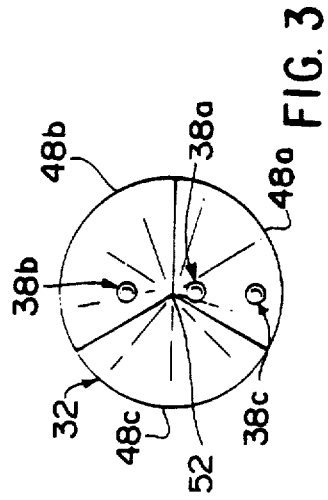
Figure 4:
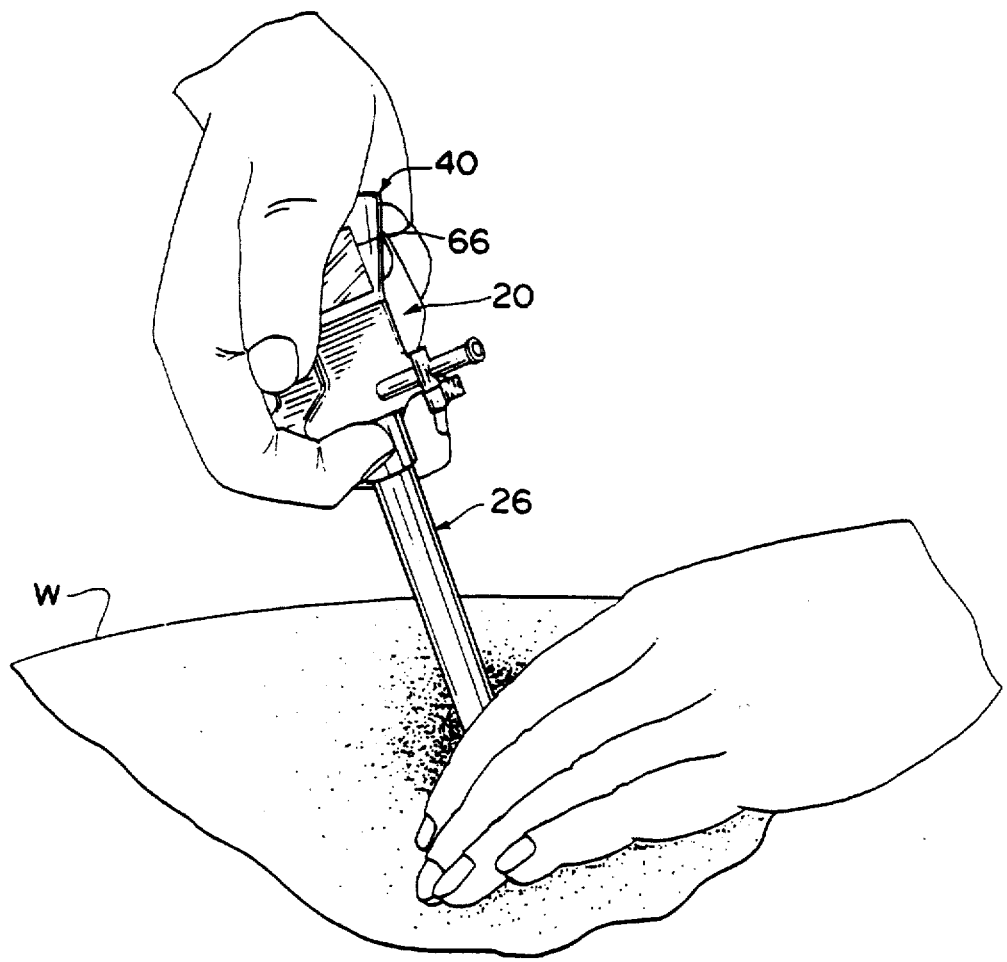
Figure 5:
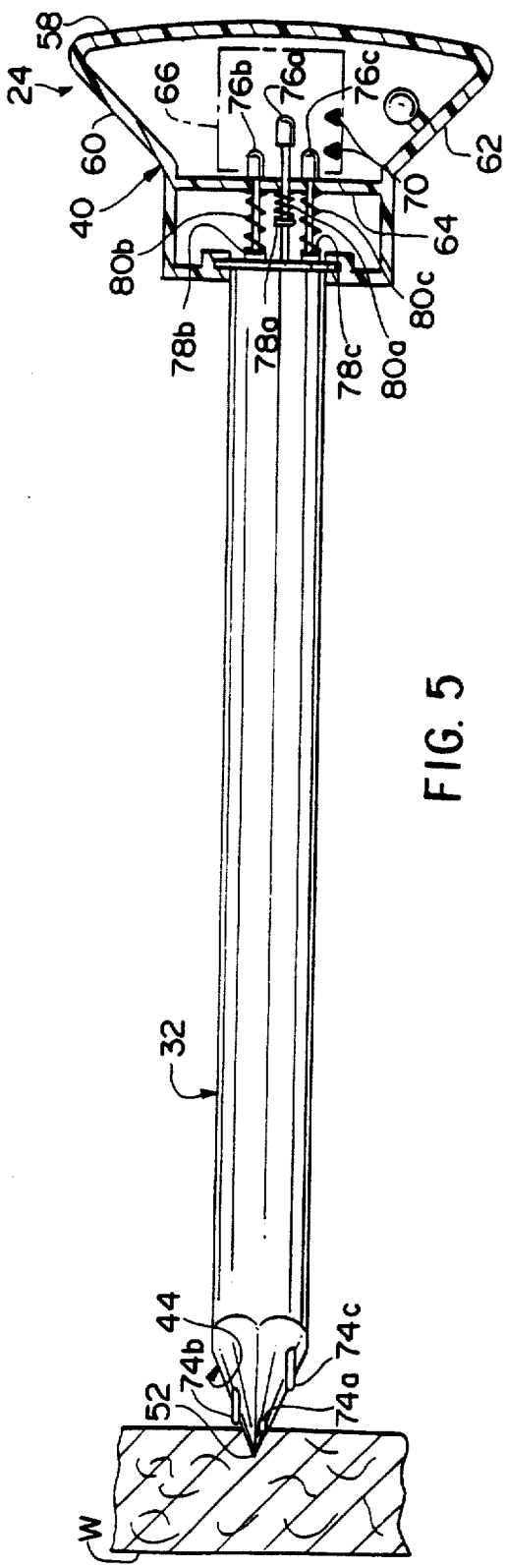
Figure 6:
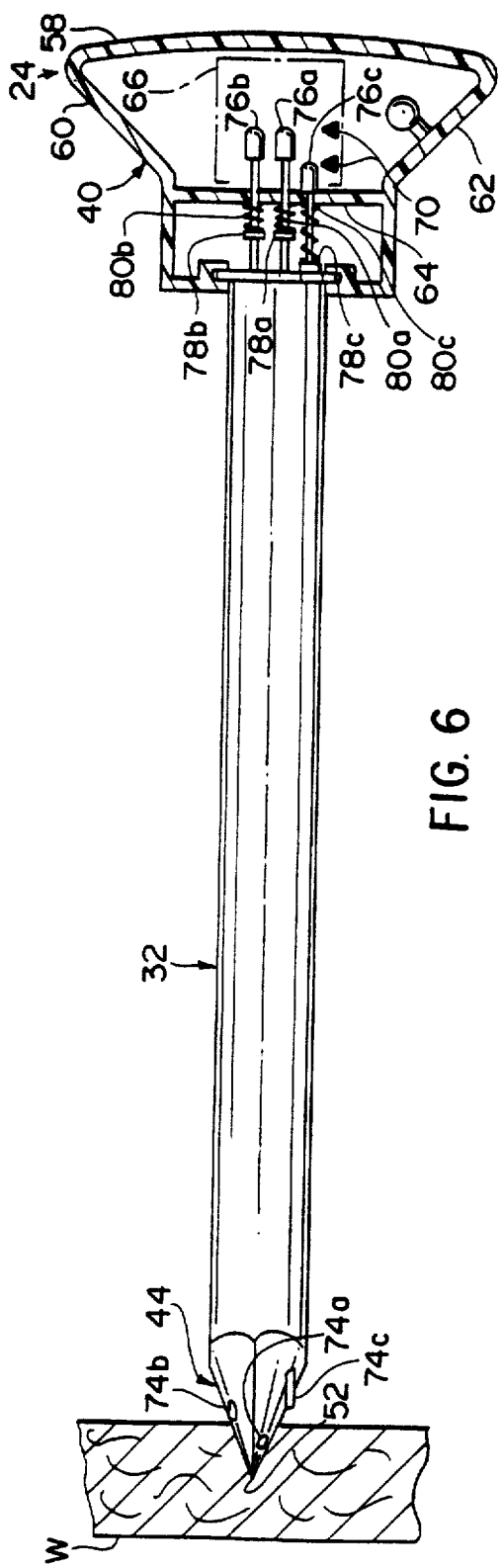
Figure 7:
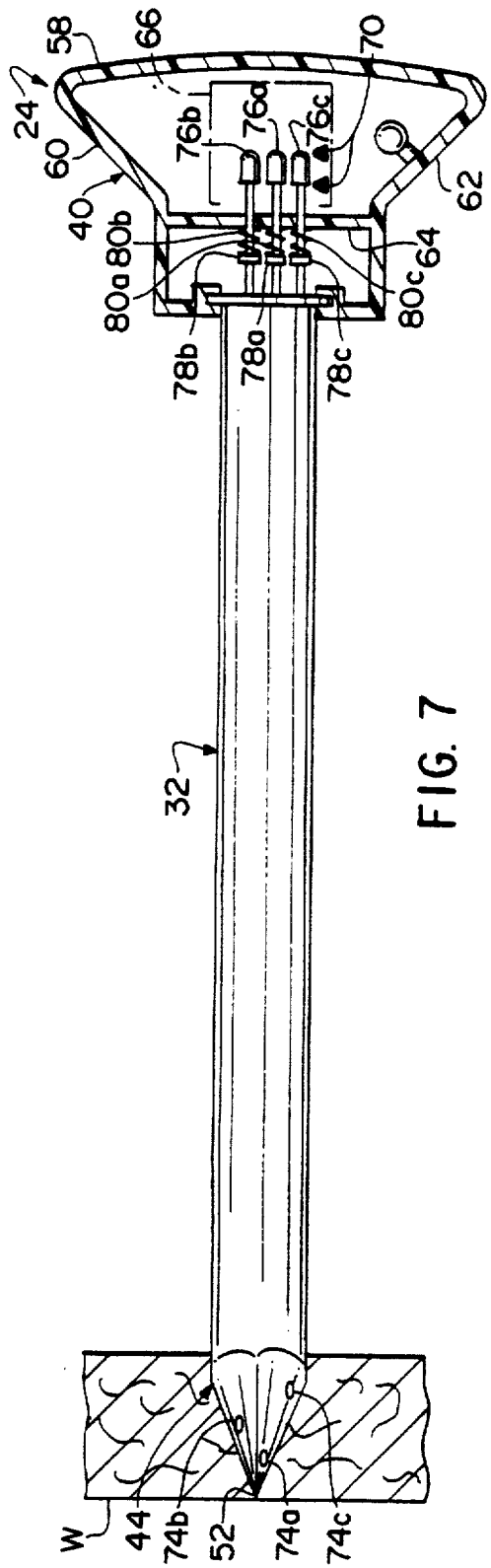
Figure 8:
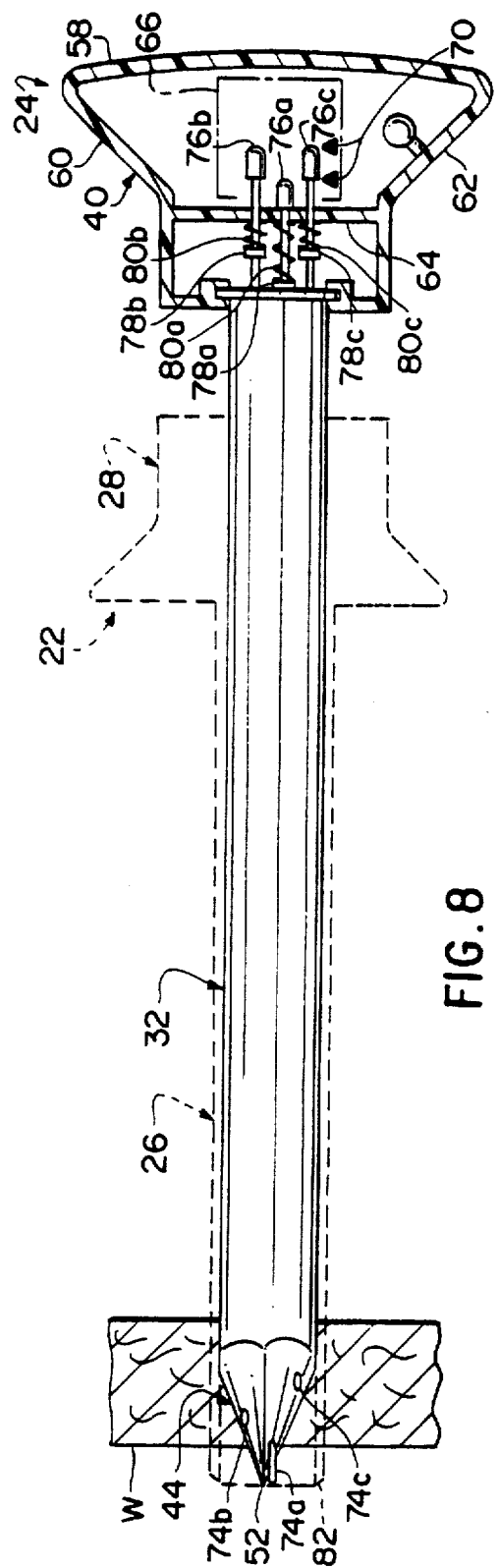
Figure 9:
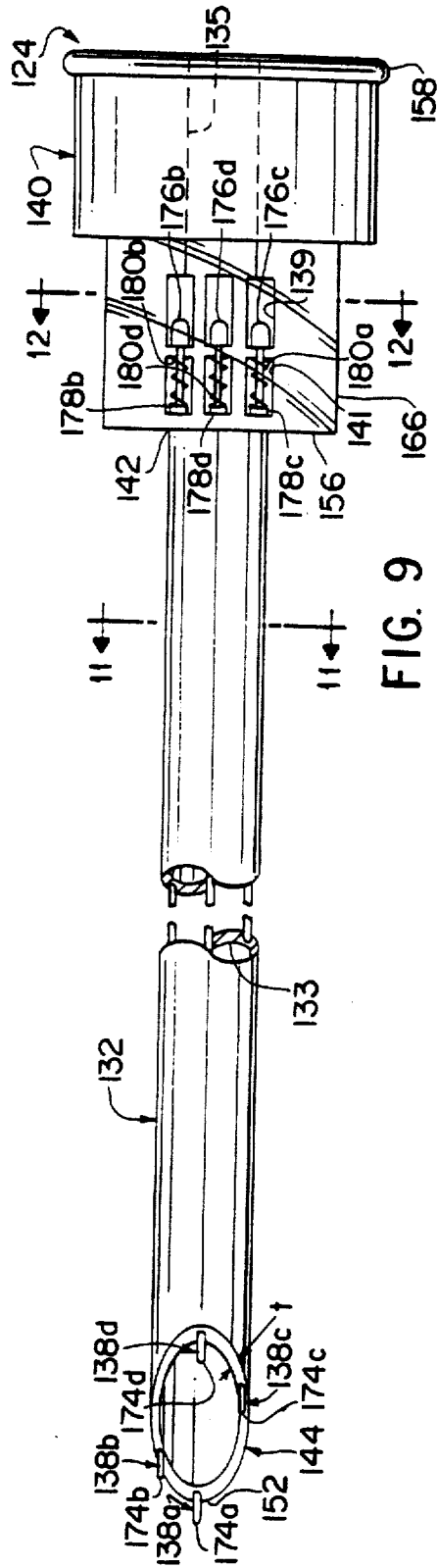
Figure 10:
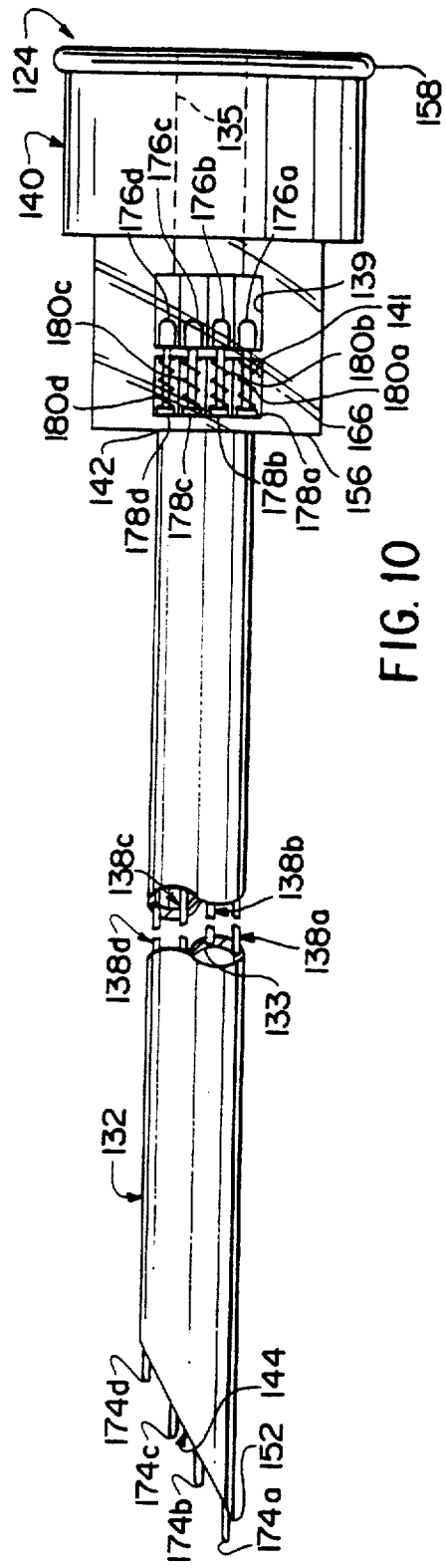
Figure 11:
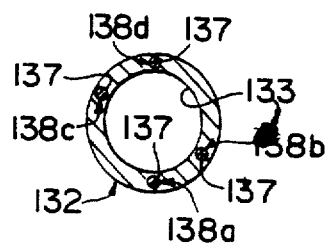
Figure 12:
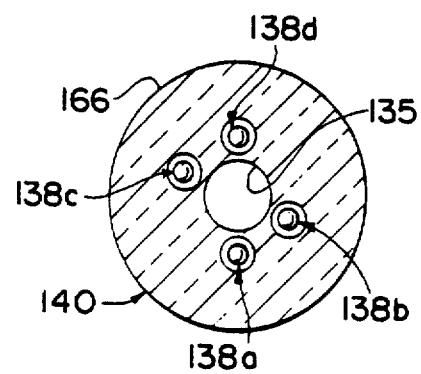
Figure 13:
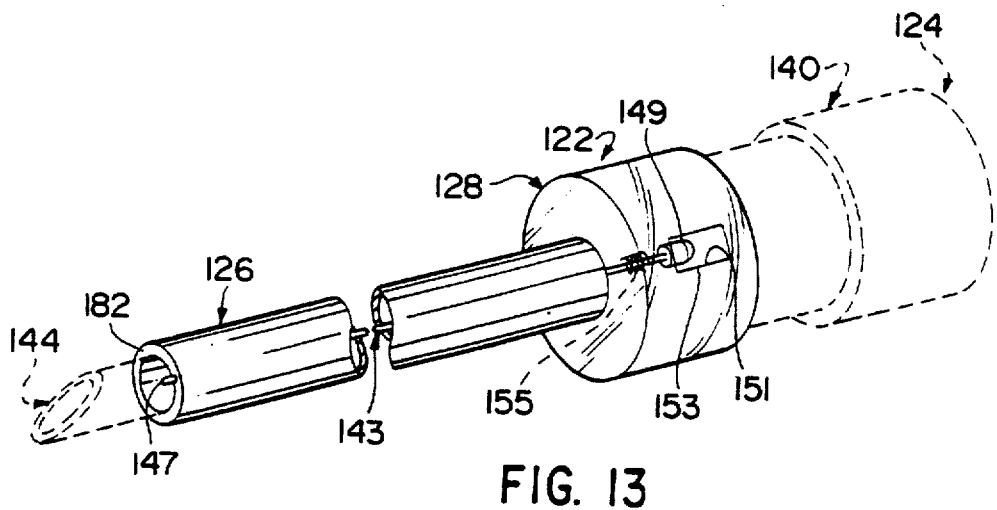
Figure 14:
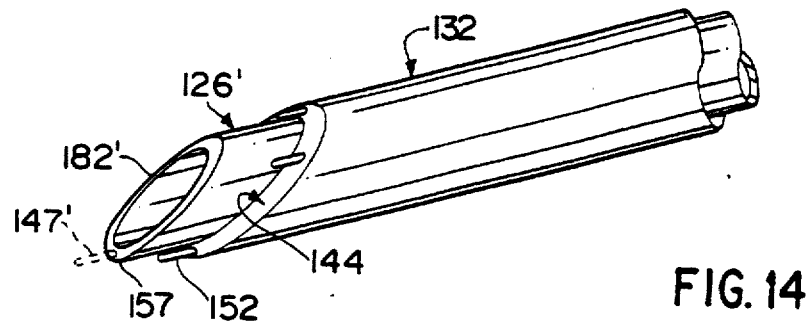

A cannula, catheter or portal sleeve 126' can also be disposed concentrically within the needle 132 of penetrating unit 124 as shown in FIG. 14 to function as a safety member upon penetration of the needle into an anatomical cavity. Catheter 126' is tubular and hollow with a beveled distal end 182' having a rounded or blunt tip 157 to protect tissue and organ structures in or forming the anatomical cavity. The catheter is distally biased to protrude from the distal end 144 of the needle 132 in an extended position and to move proximally toward a retracted position aligned with the penetrating member distal end 144 in response to the force from tissue contact during penetration. Upon penetrating into the anatomical cavity, the force from tissue contact with the catheter 126' is reduced or removed permitting the catheter to be moved distally to the extended position shown where it protects tissue and organ structures from inadvertent contact with the sharp tip 152 of the needle. The penetrating unit 124 can then be left in place with the portal unit or withdrawn from the portal unit leaving the catheter 126' in place to serve as a portal through the anatomical cavity wall. It will be appreciated that catheter 126' can also carry a probe 147', similar to probe 147, for indicating penetration by the catheter into the anatomical cavity as shown by broken lines in FIG. 14.

Yet another modification of the penetrating instrument according to the present invention is shown in FIGS. 15 and 16 wherein the penetrating unit 224 includes a sensor or probe in the form of a spring strip 201. Spring strip 201 is preferably made of a strip of resilient material formed to have a straight central portion 202 disposed within the penetrating member along a longitudinal axis thereof, an enlarged proximal portion or button 203 and a laterally expandable or extendable distal portion or end 204. Extendable distal portion 204 is biased in a direction radially outward or transverse to the longitudinal axis of the penetrating member so as to be normally disposed in the laterally extended position shown in FIG. 15. In the laterally extended position, the extendable distal portion 204 of the spring strip forms a generally U-shaped projection having a first leg 205 extending at an angle from straight central portion 202 to a bend or apex 206 disposed outwardly of the periphery, circumference or cross-section of the penetrating member distal end 244, and a second leg 207 extending inwardly from the apex to be fixed to an inside surface of the penetrating member. A slot or opening 208 is formed at the penetrating member distal end 244 to permit passage of the extendable distal portion or end of the probe through the penetrating member in the extended position.

Central portion 202 of the spring strip probe passes through longitudinally spaced eyelets 209 and 210 mounted on an inside surface of the penetrating member to permit sliding movement of the central portion of the spring strip within the penetrating member when the extendable distal portion 204 is depressed or flattened and to assure axial alignment of the button 203 at the proximal end of the spring strip with indicia or markings 270 beneath the translucent or transparent window portion 266 of the hub 240. Indicia 270 are shown as a pair of axially spaced arrowheads with the distance between the arrowheads preferably corresponding to the axial extension resulting from depression or flattening of the laterally extendable portion. Since the distal end of the spring strip is fixed, it will be appreciated that depression or flattening of extendable portion 204 of the spring strip causes an axial extension of the spring strip in the proximal direction; and, as best seen in FIG. 15, when extendable portion 204 is in the laterally extended position, button 203 of the spring strip is disposed adjacent the distalmost arrowhead of indicia 270.

The outward bias for extendable portion 204 can be selected to permit movement of the extendable portion inwardly toward the instrument longitudinal axis in the lateral, radial or transverse direction from the extended position to the retracted position shown in FIG. 16 in response to a lateral resistance or force from anatomical tissue during penetration of an anatomical cavity wall and to permit movement of the extendable portion outwardly in the lateral, radial or transverse direction from the retracted position to the extended position in response to a decrease, reduction or removal of the lateral resistance or force upon penetration into the cavity. In the retracted position, extendable portion 204 is flattened or straightened so as to be disposed substantially parallel to or in alignment with the longitudinal axis of the instrument such that the extendable portion has an axial length in the retracted position greater than the length of the extendable portion in the extended position. Accordingly, movement of extendable portion 204 from the extended to the retracted position causes the central portion of the spring strip and, therefore button 203 at the proximal end of the central portion, to move proximally relative to penetrating member 232 such that button 203 will be disposed adjacent the proximal arrowhead of indicia 270 as shown in FIG. 16, and movement of extendable portion 204 from the retracted position to the extended position causes central portion 202 and button 203 to move distally relative to the penetrating member. Additionally, in the retracted position, the radius, height or lateral extent of the extendable portion is aligned or substantially aligned with the periphery, circumference or cross-section of the penetrating member distal end to facilitate passage of the penetrating member through anatomical tissue.

The outward bias for extendable portion 204 can be provided in many various ways such as by forming the spring strip of a resilient material or a material having shape memory, such that the outward bias is provided by the spring strip itself, or by utilizing a separate bias device disposed between the spring strip and an inside surface of the penetrating member. Alternatively, the outward bias for extendable portion 204 can be provided by forming the spring strip of multiple pivoting segments or linkages and biasing the segments using torsion springs or the like. The extendable portion 204 could also be formed by a button or plunger biased to protrude laterally from the penetrating member and coupled by means of cams or gears with the central portion of the spring strip to produce axial or longitudinal movement of the spring strip in response to lateral movement of the button.

When a surgeon desires to penetrate into an anatomical cavity using the penetrating unit 224, the distal end 244 of the penetrating member protrudes beyond the distal end of a portal sleeve, catheter or cannula of a portal unit and spring strip 201 is in the extended position wherein extendable portion 204 protrudes laterally beyond the outer circumference, periphery or cross-section of the penetrating member distal end 244. When the sharp distal end 244 of the penetrating member is brought into contact with tissue forming an anatomical cavity wall W, a force from the anatomical tissue surrounding the penetrating member distal end will depress, flatten or contract the extendable portion 204 of spring strip 201 causing movement of the extendable portion from the extended position to the retracted position as shown in FIG. 16 to facilitate movement of penetrating member through the anatomical cavity wall. Movement of extendable portion 204 from the extended position to the retracted position causes longitudinal or axial movement of central portion 202 in a proximal direction until the button 203 at the proximal end of the spring strip is aligned with the proximal arrowhead of indicia 270. Once the extendable portion 204 has passed through the anatomical cavity wall W, the force from tissue contact will be reduced, decreased or removed permitting extendable portion 204 to move from the retracted position to the extended position due to the bias of the spring strip as shown in FIG. 15. Movement of extendable portion 204 from the retracted position to the extended position causes longitudinal or axial distal movement of central portion 202 relative to the penetrating member such that the button 203 at the proximal end of the spring strip will be disposed adjacent the distal arrowhead of indicia 270. It will be appreciated that a plurality of such spring strips can be arranged within a penetrating member with extendable portions at axially spaced locations along the penetrating member distal end to provide an incremental or sequential indication of the progress of entry into an anatomical cavity.

From the above, it will be appreciated that the penetrating instrument of the present invention utilizes mechanical movement of probes disposed at the distal end of a penetrating member to provide visual, audible and tactile signals to a surgeon indicative of the progress of entry into an anatomical cavity. Any number of probes can be used depending upon space requirements and the need for accuracy in indicating the progress or extent of entry into the anatomical cavity. The indicating portion or button at the proximal end of each probe can be distinctively shaped or color coded to attract the attention of the surgeon and can carry lights or LEDs of fixed or changeable color to further facilitate visualization during penetration of an anatomical cavity. Alternatively, the probes can contact switches in their respective extended and/or retracted positions to activate audible or visual alarms indicative of progress of entry into the anatomical cavity. The markings or indicia in the hub can take the form of scale markings, arrowheads, written words or symbols, or colored strips that are exposed when the probes are in their respective extended positions and covered as the probes are retracted. Also, portions of each probe other than the button can be color coded.

The probes can be of different length in accordance with their location within the penetrating member or the probes can all be of the same length with proximal ends of the probes travelling different distances during penetration of the anatomical cavity wall.

The translucent or transparent portions of the penetrating instrument can be positioned anywhere on the instrument to provide visual access to the surgeon of the indicating portions or buttons of the probes, and the translucent or transparent portions can be planar or curved or partially planar and curved depending upon the desirability of presenting an undistorted or magnified view of the buttons.

Inasmuch as the present invention is subject to many variations, modifications and changes in detail, it is intended that all subject matter discussed above or shown in the accompanying drawings be interpreted as illustrative only and not be taken in a limiting sense.

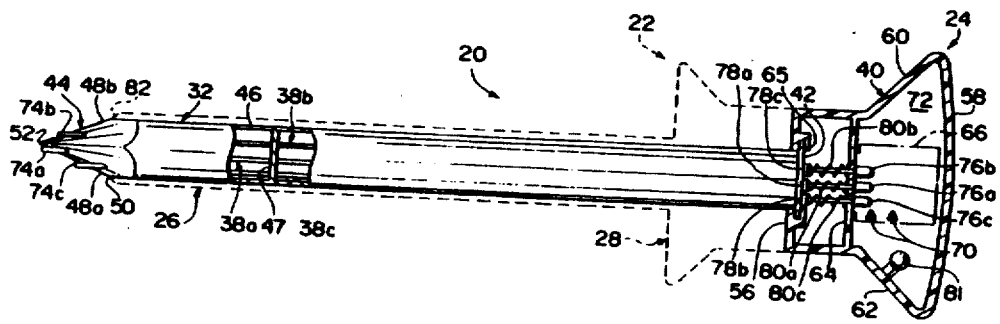

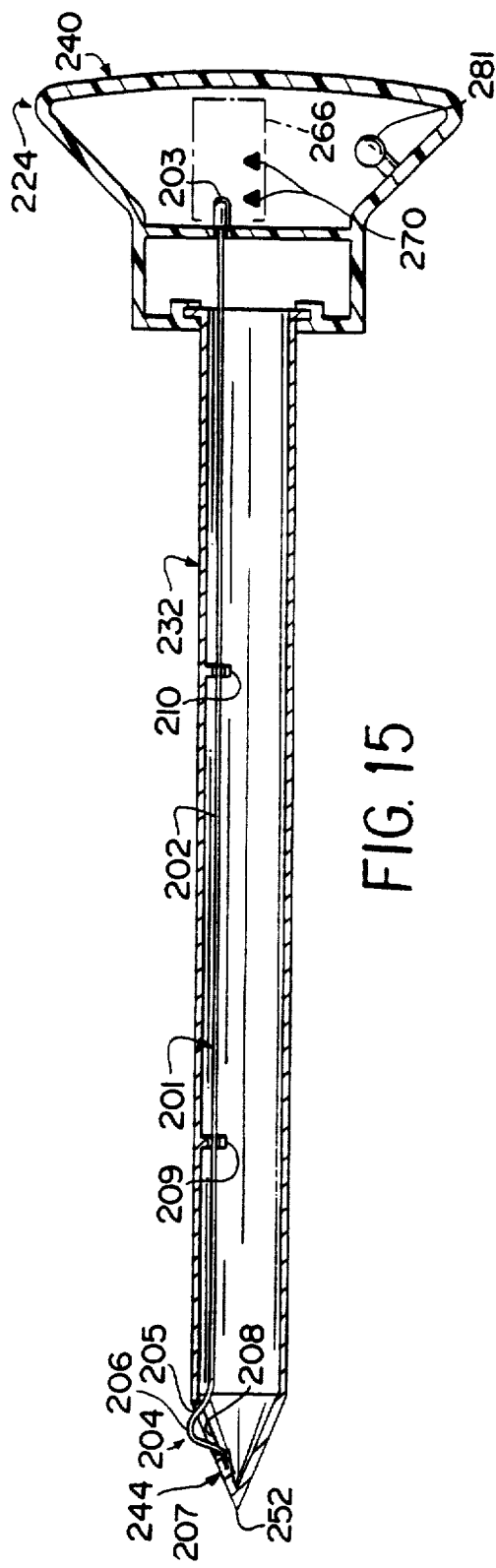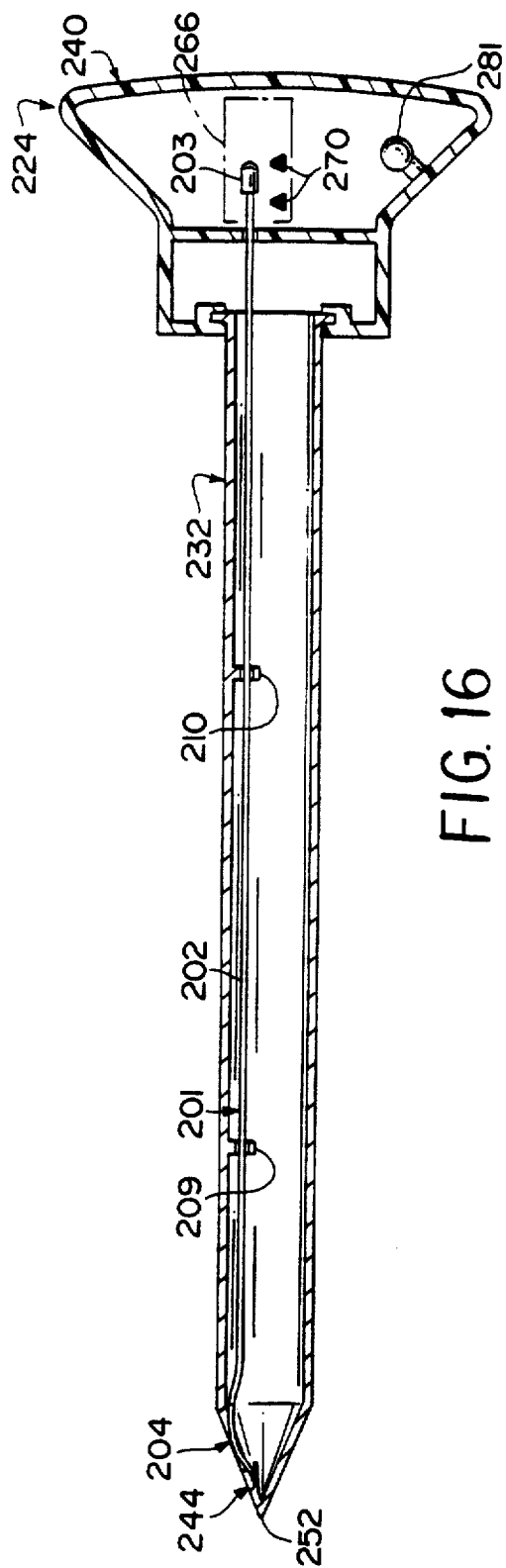

What is claimed is:

1. A penetrating instrument for penetrating an anatomical cavity wall to gain access to the anatomical cavity comprising a penetrating member having a distal end for penetrating the anatomical cavity wall;

a plurality of probes disposed in said penetrating member, each of said probes having a distal end movable relative to said penetrating member between an extended position where said distal end of said probe protrudes from said distal end of said penetrating member and a retracted position where said distal end of said probe recedes into said penetrating member, wherein respective distal ends of said probes in said retracted positions are disposed at a respective plurality of axially spaced locations along said distal end of said penetrating member;

bias means for biasing said distal ends of said probes toward said extended positions while permitting respective distal ends of said probes to move sequentially from said extended positions to said retracted positions during penetration so that, as said distal end of said penetrating member enters the anatomical cavity, respective distal ends of said probes will move sequentially from said retracted positions to said extended positions; and indicating means operatively associated with said probes for displaying a sequence of sensible signals in response to the sequential movement of said respective distal ends of said probes during penetration of the anatomical cavity wall.

2. A penetrating instrument as recited in claim 1 wherein said penetrating member has a proximal end and further comprising a hub mounting said proximal end of said penetrating member, and wherein said probes each have a proximal end, at least a portion of said hub being transparent so that said proximal ends of said probes are visible through said transparent portion of said hub during penetration of the anatomical cavity wall.

3. A penetrating instrument as recited in claim 2 and further comprising a plurality of colored heads mounted on said proximal ends of said probes.

4. A penetrating instrument as recited in claim 3 and further comprising indicia visible through said transparent portion of said hub, said indicia providing a reference against which movement of said probes can be measured.

5. A penetrating instrument as recited in claim 4 wherein said indicia includes a colored region visible when at least one of said probes is in said extended position and covered when all of said probes are in said retracted positions.

6. A penetrating instrument as recited in claim 1 wherein each of said probes is formed of an elongate rod extending longitudinally through said penetrating member and said bias means biases each rod in a distal direction toward said extended position where said distal end of said probe protrudes distally from said distal end of said penetrating member.

7. A penetrating instrument as recited in claim 6 wherein said penetrating member includes a needle having a tubular wall with longitudinal passages formed therethrough and said rods are disposed within said longitudinal passages.

8. A penetrating instrument as recited in claim 7 wherein said needle includes a beveled distal end with a peripheral edge and said passages define apertures along said peripheral edge at axially spaced locations.

9. A penetrating instrument as recited in claim 8 and further comprising a cannula disposed within said penetrating member.

10. A penetrating instrument as recited in claim 9 wherein said cannula has a tubular wall with a distal end and further comprising a probe disposed in said wall of said cannula, said probe having a distal end movable relative to said cannula between an extended position where said distal end of said probe protrudes from said distal end of said cannula and a retracted position where said distal end of said probe recedes into said cannula.

11. A penetrating instrument as recited in claim 10 and further comprising bias means for biasing said cannula probe toward said extended position.

12. A penetrating instrument as recited in claim 11 wherein said cannula has a proximal end, at least a portion of which is transparent, and wherein a portion of said probe is visible through said transparent portion of said proximal end of said cannula.

13. A penetrating instrument as recited in claim 1 wherein said distal end of said penetrating member is defined by a substantially solid penetrating surface and further comprising apertures formed through said penetrating surface at axially spaced locations along said penetrating surface, said probes extending through said apertures.

14. A penetrating instrument as recited in claim 13 wherein said penetrating surface is pyramidal and said probes are diametrically spaced across said penetrating surface.

15. A penetrating instrument as recited in claim 13 and further comprising a cannula disposed concentrically around said penetrating member.

16. A penetrating instrument as recited in claim 15 wherein said cannula has a tubular wall with a distal end and further comprising a probe disposed in said wall of said cannula, said probe having a distal end movable relative to said cannula between an extended position where said distal end of said probe protrudes from said distal end of said cannula and a retracted position where said distal end of said probe recedes into said cannula.

17. A penetrating instrument as recited in claim 16 and further comprising bias means for biasing said cannula probe toward said extended position.

18. A penetrating instrument as recited in claim 17 wherein said cannula has a proximal end, at least a portion of which is transparent, and wherein a portion of said probe is visible through said transparent portion of said proximal end of said cannula.

19. A penetrating instrument for penetrating an anatomical cavity wall to gain access to the anatomical cavity comprising a penetrating member having a distal end for penetrating the anatomical cavity wall;

a plurality of probes disposed in said penetrating member, each of said probes having a distal end movable relative to said penetrating member between an extended position where said distal end of said probe protrudes from said distal end of said penetrating member and a retracted position where said distal end of said probe recedes into said penetrating member, wherein respective distal ends of said probes in said retracted positions are at axially spaced locations along said distal end of said penetrating member, wherein each of said probes is formed of a spring strip having a distal end with an expandable portion biased outwardly of said penetrating member in a lateral direction transverse to a longitudinal axis of said penetrating member, said expandable portions extending through axially spaced openings formed in said penetrating member distal end;

bias means for biasing said distal ends of said probes toward said extended positions; and indicating means operatively associated with said probes for displaying a sequence of sensible signals in response to movement of said respective distal ends of said probes during penetration of the anatomical cavity wall.

20. A method of forming a portal in the wall of an anatomical cavity comprising the steps of penetrating the anatomical cavity wall with a penetrating member of a penetrating instrument having a plurality of probes protruding from a distal end of the penetrating member at axially spaced locations;

biasing each probe to an extended position where a distal end of the probe protrudes outwardly of the penetrating member distal end;

permitting the probes to move sequentially from the extended positions to retracted positions within the penetrating member during penetration of the anatomical cavity wall and from the retracted positions to the extended positions as the distal end of the penetrating member enters the anatomical cavity; and indicating progress of entry into the anatomical cavity by displaying a sequence of sensible signals in response to the sequential movement of the probes during penetration of the anatomical cavity wall.

21. A method of forming a portal in the wall of an anatomical cavity as recited in claim 20 wherein said indicating step includes displaying movement of proximal ends of the probes.

22. A method of forming a portal in the wall of an anatomical cavity as recited in claim 21 and further comprising the step of viewing movement of the proximal ends of the probes through a window formed in a hub of the penetrating instrument.

23. A method of forming a portal in the wall of an anatomical cavity as recited in claim 22 and further comprising the step of suspending penetration of the anatomical cavity in response to movement of a probe from the retracted position to the extended position caused by a reduction in force from tissue contact.

24. A method of forming a portal in the wall of an anatomical cavity as recited in claim 23 and further comprising, after said suspending step, the step of advancing a cannula over the penetrating member into the anatomical cavity.

* * * * *

UNITED STATES PATENT AND TRADEMARK OFFICE
CERTIFICATE OF CORRECTION

PATENT NO. : 5,571,133
DATED : November 5, 1996
INVENTOR(S) : InBae Yoon

It is certified that error appears in the above-indentified patent and that said Letters Patent is hereby corrected as shown below:

Title page, showing an illustrative figure should be deleted and substitute therefor the attached title page.

Drawings:

Delete drawing sheets 1-8 consisting of Figs. 1-16 and substitute therefore the attached sheets.

Signed and Sealed this

Third Day of June, 1997

Attest:

BRUCE LEHMAN

*Attesting Officer*     Commissioner of Patents and Trademarks

United States Patent [19]

Yoon

[11] Patent Number: 5,571,133
[45] Date of Patent: Nov. 5, 1996

[54] PENETRATING INSTRUMENT WITH SEQUENTIAL INDICATION OF ENTRY INTO ANATOMICAL CAVITIES

[76] Inventor: InBae Yoon, 2101 Highland Ridge Dr., Phoenix, Md. 21131

[21] Appl. No.: 457,527

[22] Filed: Jun. 1, 1995

[51] Int. Cl.⁶ ............................................. A61B 17/34
[52] U.S. Cl. ........................ 606/185; 604/164; 604/264
[58] Field of Search ........................ 606/185; 604/264, 604/164

[56] References Cited

U.S. PATENT DOCUMENTS

| | | | |
|---|---|---|---|
| 4,186,750 | 2/1980 | Patel | 128/748 |
| 4,215,699 | 8/1980 | Patel | 128/748 |
| 4,299,230 | 11/1981 | Kubota | 128/630 |
| 4,356,826 | 11/1982 | Kubota | 128/630 |
| 4,535,773 | 8/1985 | Yoon | 604/51 |
| 5,226,426 | 7/1993 | Yoon | 604/169 X |
| 5,275,583 | 1/1994 | Crainich | 604/167 |
| 5,292,310 | 3/1994 | Yoon | 604/158 |
| 5,336,176 | 8/1994 | Yoon | 604/164 X |
| 5,336,206 | 8/1994 | Shichman | 604/283 |
| 5,352,206 | 10/1994 | Cushieri et al. | 604/164 |
| 5,385,572 | 1/1995 | Nobles et al. | 606/185 |
| 5,401,247 | 3/1995 | Yoon | 604/165 |
| 5,445,142 | 8/1995 | Hassler, Jr. | 604/164 |
| 5,454,791 | 10/1995 | Tovey et al. | 604/164 |

FOREIGN PATENT DOCUMENTS

94/27513  12/1994  WIPO ......................... 604/167

Primary Examiner—Michael Powell Buiz
Assistant Examiner—Patrick W. Rasche

[57] ABSTRACT

A penetrating instrument for penetrating an anatomical cavity wall to gain access to the anatomical cavity includes a penetrating member having a distal end for penetrating the anatomical cavity wall, a plurality of probes disposed in the penetrating member, and an indicating mechanism operatively associated with the probes for displaying a sequence of sensible signals in response to movement of the probes during penetration of the anatomical cavity wall. Each of the probes has a distal end movable relative to the penetrating member between an extended position where the distal end of the probe protrudes from the distal end of the penetrating member and a retracted position where the distal end of the probe recedes into the penetrating member. In the retracted positions, respective distal ends of the probes are at axially spaced locations along the distal end of the penetrating member such that movement of the probes from the extended positions to the retracted positions occurs sequentially in response to penetration of the anatomical cavity wall by the penetrating member, and movement of the probes from the retracted positions to the extended positions occurs sequentially in response to penetration into the anatomical cavity by the penetrating member.

24 Claims, 8 Drawing Sheets